(12) United States Patent
Griffin

(10) Patent No.: US 9,662,173 B1
(45) Date of Patent: May 30, 2017

(54) LATERAL DELIVERY DEVICE WITH ACTIVE COOLING

(71) Applicant: Cyclone Biosciences LLC, Phoenix, AZ (US)

(72) Inventor: Stephen E. Griffin, Peoria, AZ (US)

(73) Assignee: Cyclone Biosciences LLC, Phoenix, AZ (US)

( * ) Notice: Subject to any disclaimer, the term of this patent is extended or adjusted under 35 U.S.C. 154(b) by 0 days.

(21) Appl. No.: 15/382,611

(22) Filed: Dec. 17, 2016

Related U.S. Application Data

(60) Provisional application No. 62/387,475, filed on Dec. 24, 2015.

(51) Int. Cl.
| | |
|---|---|
| *A61B 18/24* | (2006.01) |
| *A61B 18/22* | (2006.01) |
| *G02B 6/32* | (2006.01) |
| *G02B 6/26* | (2006.01) |
| *A61B 18/00* | (2006.01) |

(52) U.S. Cl.
CPC .............. *A61B 18/24* (2013.01); *G02B 6/262* (2013.01); *G02B 6/32* (2013.01); *A61B 2018/00023* (2013.01); *A61B 2018/00172* (2013.01); *A61B 2018/00547* (2013.01); *A61B 2018/00625* (2013.01); *A61B 2018/2272* (2013.01)

(58) Field of Classification Search
CPC .................. A61B 2018/2272; A61B 18/24
See application file for complete search history.

(56) References Cited

U.S. PATENT DOCUMENTS

| | | | |
|---|---|---|---|
| 4,669,467 A | 6/1987 | Willett et al. |
| 4,672,961 A | 6/1987 | Davies |
| 4,718,417 A | 1/1988 | Kittrell et al. |
| 4,732,448 A | 3/1988 | Goldenberg |
| 4,740,047 A | 4/1988 | Abe et al. |
| 4,842,390 A | 6/1989 | Sottini et al. |
| 4,967,745 A | 11/1990 | Hayes et al. |
| 5,019,075 A | 5/1991 | Spears et al. |
| 5,061,265 A | 10/1991 | Abela et al. |
| 5,074,632 A | 12/1991 | Potter |
| 5,093,877 A | 3/1992 | Aita et al. |
| 5,104,392 A | 4/1992 | Kittrell et al. |
| 5,106,387 A | 4/1992 | Kittrell et al. |
| 5,125,404 A | 6/1992 | Kittrell et al. |
| 5,192,278 A | 3/1993 | Hayes et al. |

(Continued)

*Primary Examiner* — Omar R Rojas
(74) *Attorney, Agent, or Firm* — Synthesis Intellectual Property LLC

(57) ABSTRACT

Herein is disclosed an optical device for directing electromagnetic radiation and a means for manufacturing the same. The optical device can include a total-internal-reflection (TIR) element which includes a TIR surface; a TIR protective cap fused about the TIR element, thereby providing a liquid-free volume between the TIR surface and an internal surface of the TIR protective cap; a sleeve element fused to a portion of the TIR protective cap, thereby providing at least one fluidic pathway between the sleeve element and the TIR protective cap, the at least one fluidic pathway adapted to carry a stream of a cooling fluid through the optical device during use; and an optical pathway from the TIR surface to an external surface of the sleeve element; where any of the at least one fluidic pathway does not cross the optical pathway.

15 Claims, 13 Drawing Sheets

(56) References Cited

U.S. PATENT DOCUMENTS

| | | | |
|---|---|---|---|
| 5,199,431 A | 4/1993 | Kittrell et al. |
| 5,231,684 A | 7/1993 | Narciso et al. |
| 5,242,438 A | 9/1993 | Saadatmanesh et al. |
| 5,246,436 A | 9/1993 | Rowe |
| 5,269,777 A | 12/1993 | Doiron et al. |
| 5,290,275 A | 3/1994 | Kittrell et al. |
| 5,292,320 A | 3/1994 | Brown et al. |
| 5,342,355 A | 8/1994 | Long |
| 5,343,543 A | 8/1994 | Novak et al. |
| 5,354,294 A | 10/1994 | Chou |
| 5,409,483 A | 4/1995 | Campbell et al. |
| 5,428,699 A | 6/1995 | Pon |
| 5,437,660 A | 8/1995 | Johnson et al. |
| 5,454,807 A | 10/1995 | Lennox et al. |
| 5,468,239 A | 11/1995 | Tanner et al. |
| 5,486,171 A | 1/1996 | Chou |
| 5,495,541 A | 2/1996 | Murray et al. |
| 5,496,307 A | 3/1996 | Daikuzono |
| 5,496,308 A | 3/1996 | Brown et al. |
| 5,496,309 A | 3/1996 | Saadat et al. |
| 5,498,260 A | 3/1996 | Rink et al. |
| 5,509,917 A | 4/1996 | Cecchetti et al. |
| 5,512,078 A | 4/1996 | Griffin |
| 5,530,780 A | 6/1996 | Ohsawa |
| 5,537,499 A | 7/1996 | Brekke |
| 5,562,657 A | 10/1996 | Griffin |
| 5,571,099 A | 11/1996 | Purcell et al. |
| 5,672,171 A | 9/1997 | Andrus et al. |
| 5,685,824 A | 11/1997 | Takei |
| 5,695,583 A | 12/1997 | Bergh et al. |
| 5,737,472 A | 4/1998 | Bernasson et al. |
| 5,807,390 A | 9/1998 | Fuller et al. |
| 5,824,005 A | 10/1998 | Motamedi et al. |
| 5,908,415 A | 6/1999 | Sinofsky |
| 6,102,905 A | 8/2000 | Baxter et al. |
| 6,113,589 A | 9/2000 | Levy et al. |
| 6,246,817 B1 | 6/2001 | Griffin |
| 6,270,492 B1 | 8/2001 | Sinofsky |
| 6,284,085 B1 | 9/2001 | Gwo |
| 6,302,878 B1 * | 10/2001 | Daikuzono ......... A61N 5/0601 606/15 |
| 6,398,777 B1 | 6/2002 | Navarro et al. |
| 6,398,778 B1 | 6/2002 | Gu et al. |
| 6,436,094 B1 | 8/2002 | Reuter |
| 6,522,806 B1 | 2/2003 | James et al. |
| 6,687,436 B2 | 2/2004 | Griffin |
| 6,712,526 B1 | 3/2004 | Fleenor |
| 6,802,838 B2 | 10/2004 | Loeb et al. |
| 6,829,411 B2 | 12/2004 | Easley |
| 6,893,432 B2 | 5/2005 | Intintoli et al. |
| 6,953,458 B2 | 10/2005 | Loeb |
| 6,986,764 B2 | 1/2006 | Davenport et al. |
| 7,270,656 B2 | 9/2007 | Gowda et al. |
| 7,273,478 B2 | 9/2007 | Appling et al. |
| 7,359,601 B2 | 4/2008 | Loeb |
| 7,386,203 B2 | 6/2008 | Maitland et al. |
| 7,463,801 B2 | 12/2008 | Brekke et al. |
| 7,492,987 B2 | 2/2009 | Yeik et al. |
| 7,524,316 B2 | 4/2009 | Hennings et al. |
| 7,909,817 B2 * | 3/2011 | Griffin ................. A61B 18/22 606/13 |
| 8,073,297 B2 | 12/2011 | Griffin |
| 8,211,095 B2 | 7/2012 | Gowda et al. |
| 8,257,347 B2 | 9/2012 | Neuberger |
| 8,285,097 B2 | 10/2012 | Griffin |
| 8,425,500 B2 | 4/2013 | Hanley et al. |
| 8,435,235 B2 | 5/2013 | Stevens et al. |
| 8,529,561 B2 | 9/2013 | Griffin et al. |
| 8,851,080 B2 | 10/2014 | Gowda et al. |
| 8,858,542 B2 | 10/2014 | Peng et al. |
| 8,932,289 B2 | 1/2015 | Mayse et al. |
| 9,005,195 B2 | 4/2015 | Mayse et al. |
| 9,017,324 B2 | 4/2015 | Mayse et al. |
| 9,323,005 B1 | 4/2016 | Griffin |
| 9,488,782 B2 | 11/2016 | Griffin |
| 2005/0015123 A1 | 1/2005 | Paithankar |
| 2005/0165279 A1 | 7/2005 | Adler et al. |
| 2006/0291061 A1 | 12/2006 | Iyama et al. |
| 2007/0106286 A1 | 5/2007 | Harschack et al. |
| 2008/0287936 A1 | 11/2008 | Stinson et al. |
| 2009/0240242 A1 | 9/2009 | Neuberger |
| 2010/0135617 A1 | 6/2010 | Novak et al. |
| 2010/0179525 A1 | 7/2010 | Neuberger |
| 2011/0038580 A1 | 2/2011 | Griffin |
| 2011/0282330 A1 | 11/2011 | Harschack et al. |
| 2014/0074072 A1 | 3/2014 | Griffin et al. |
| 2015/0057648 A1 | 2/2015 | Swift et al. |

* cited by examiner

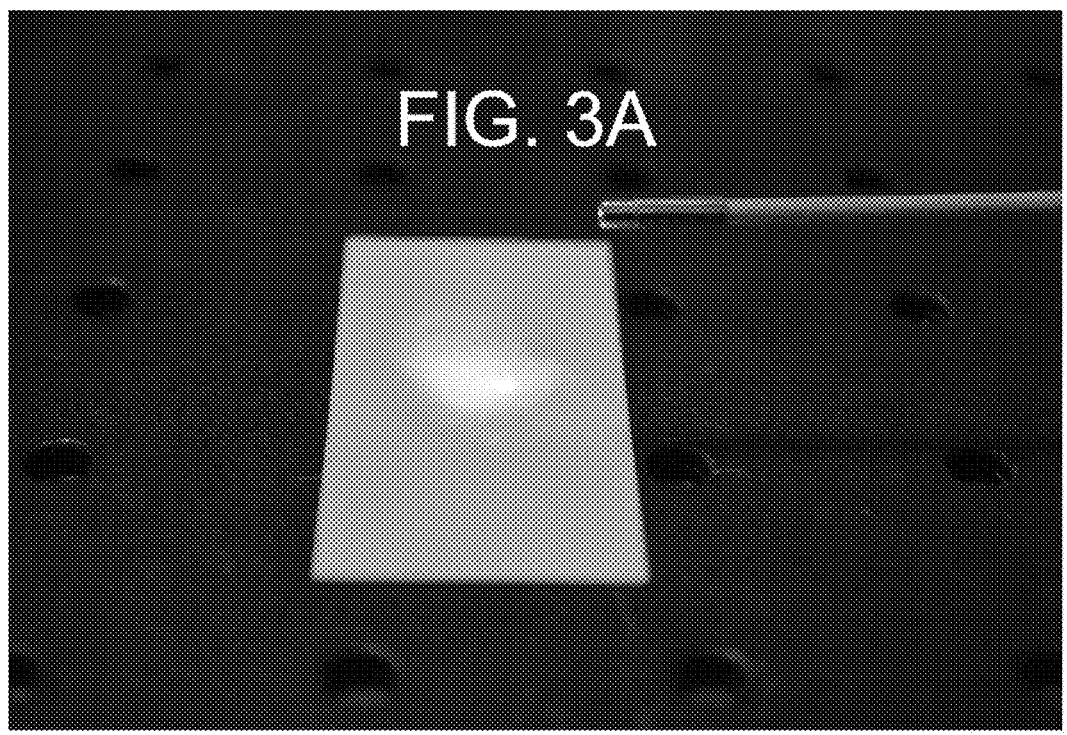
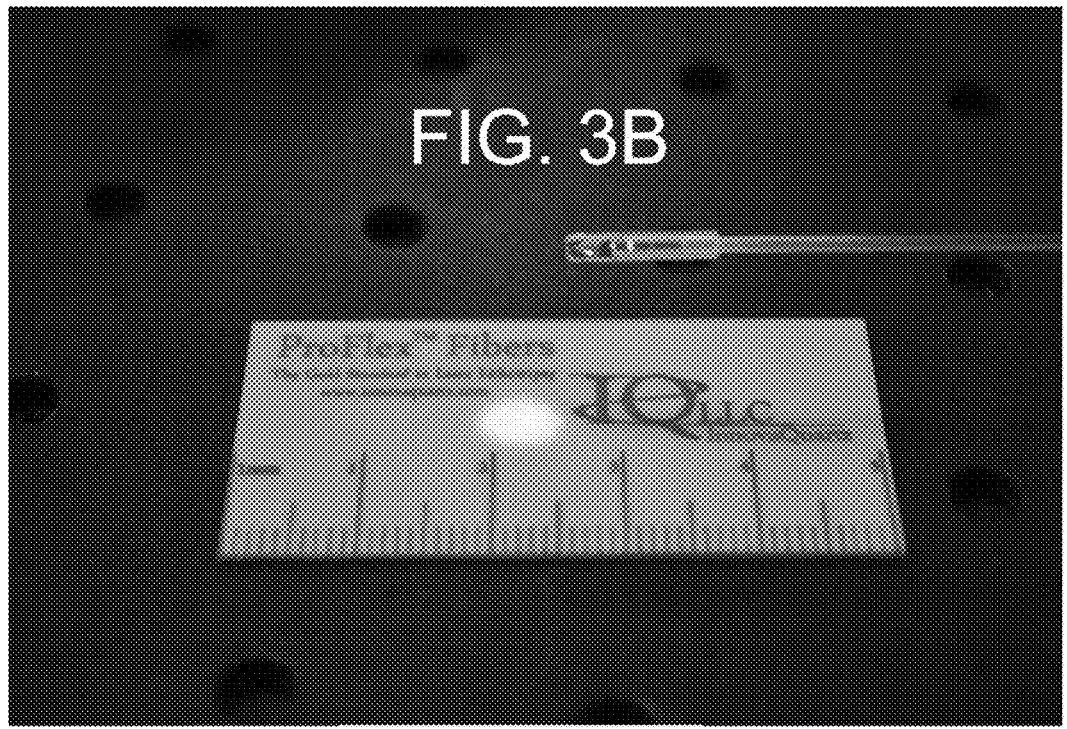

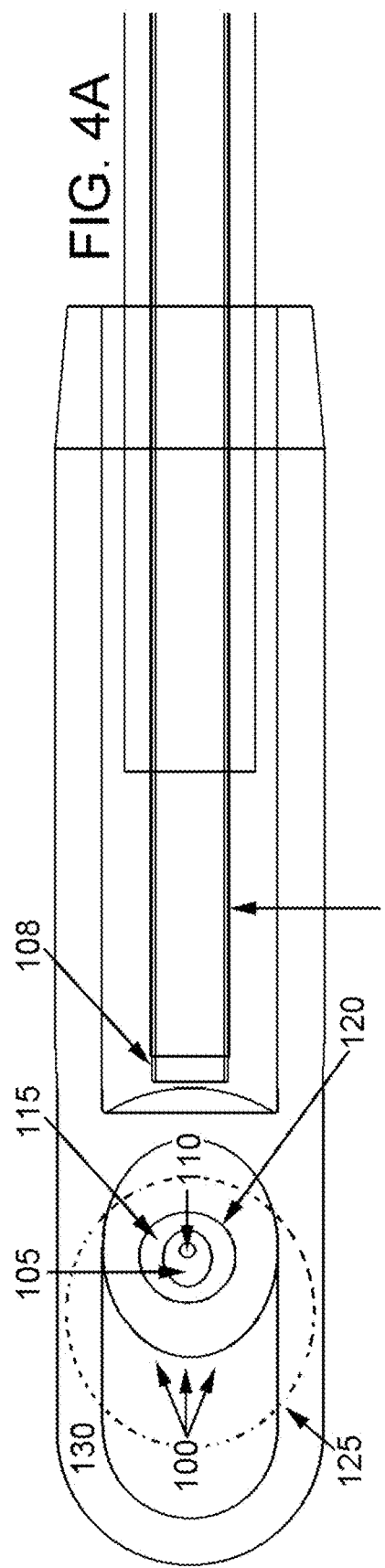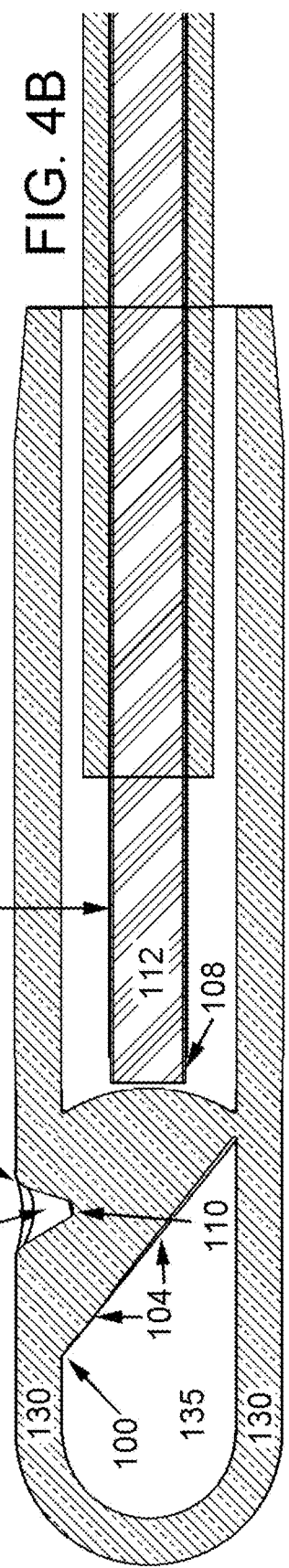

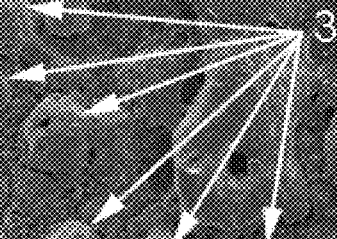

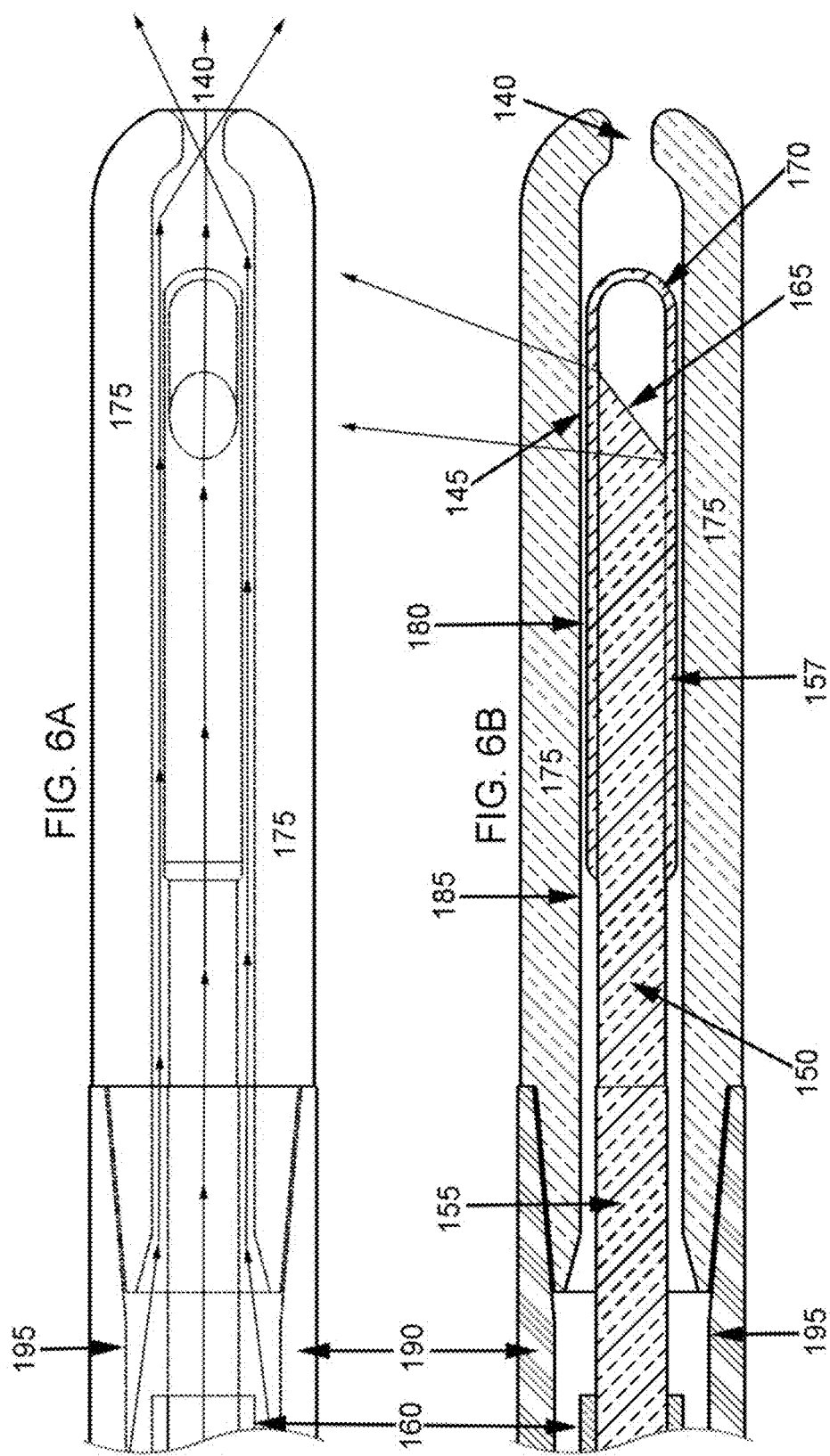

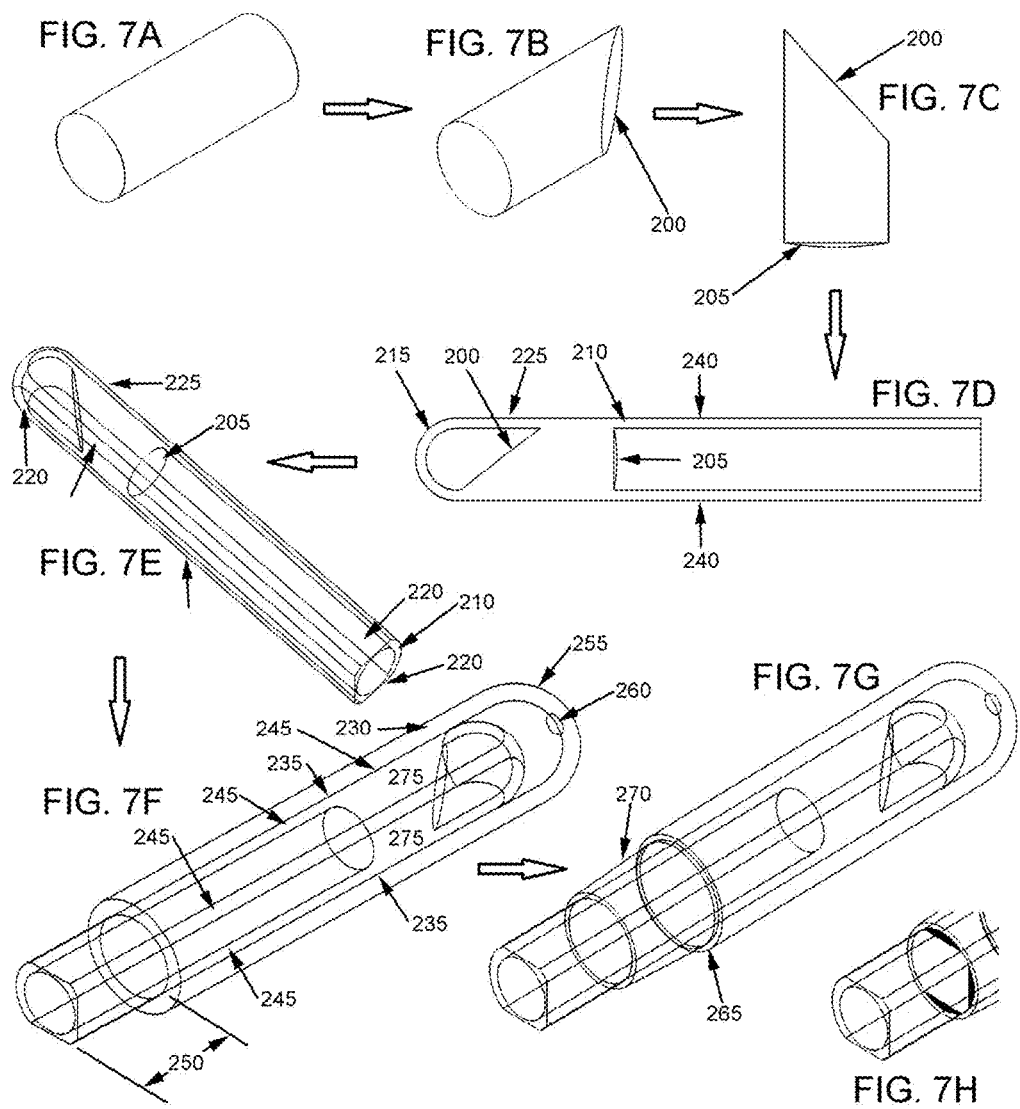

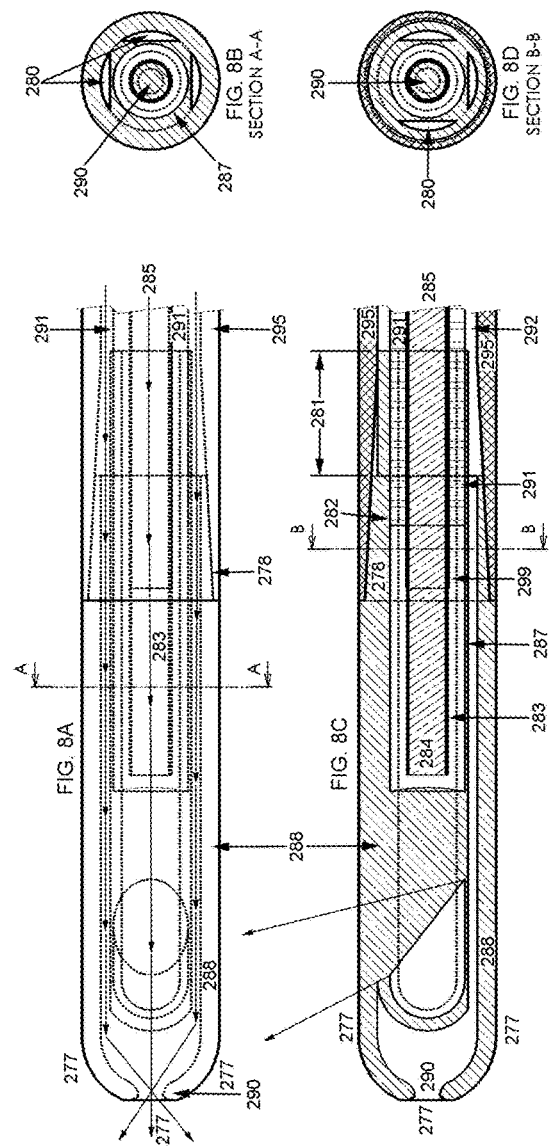

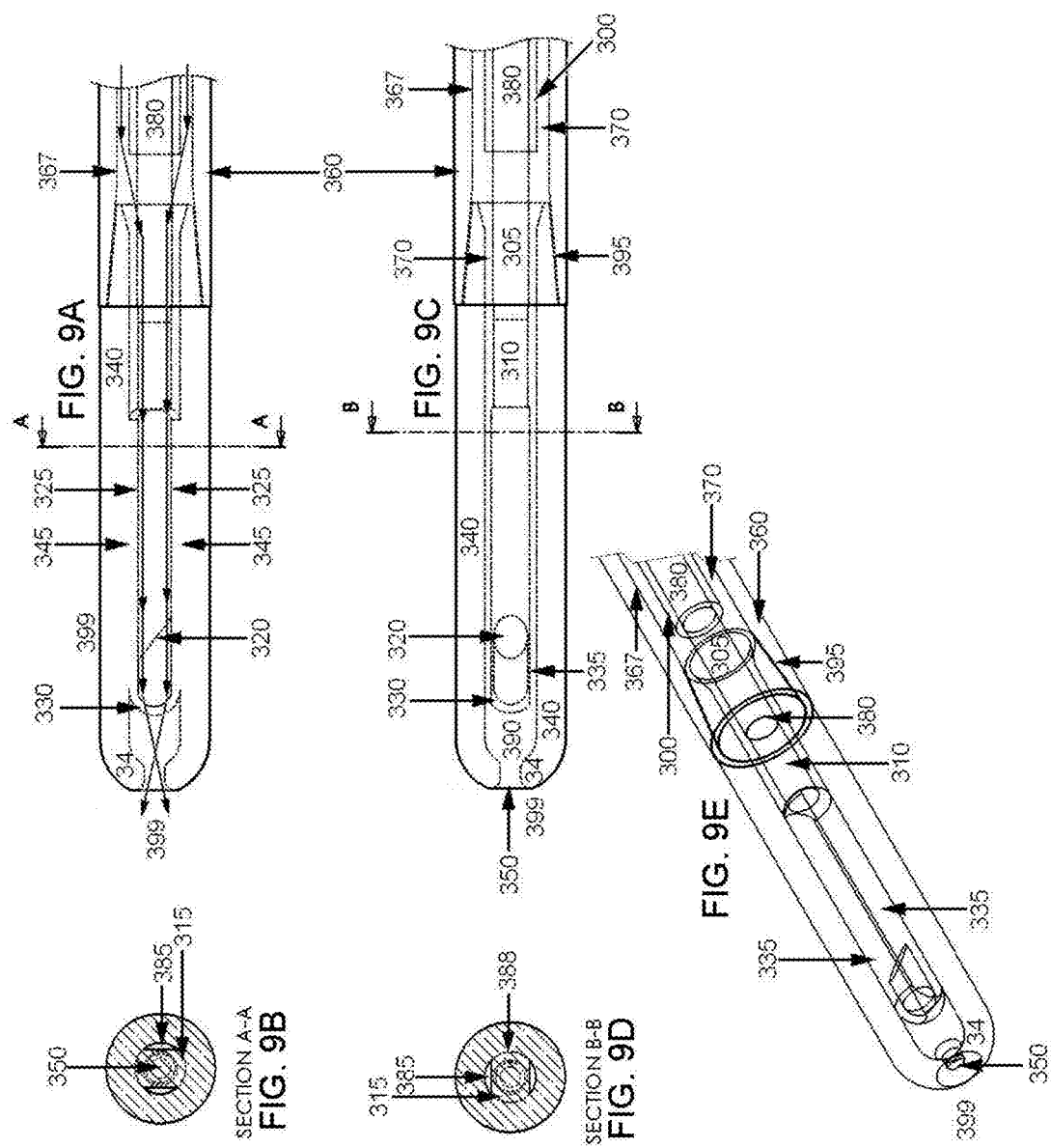

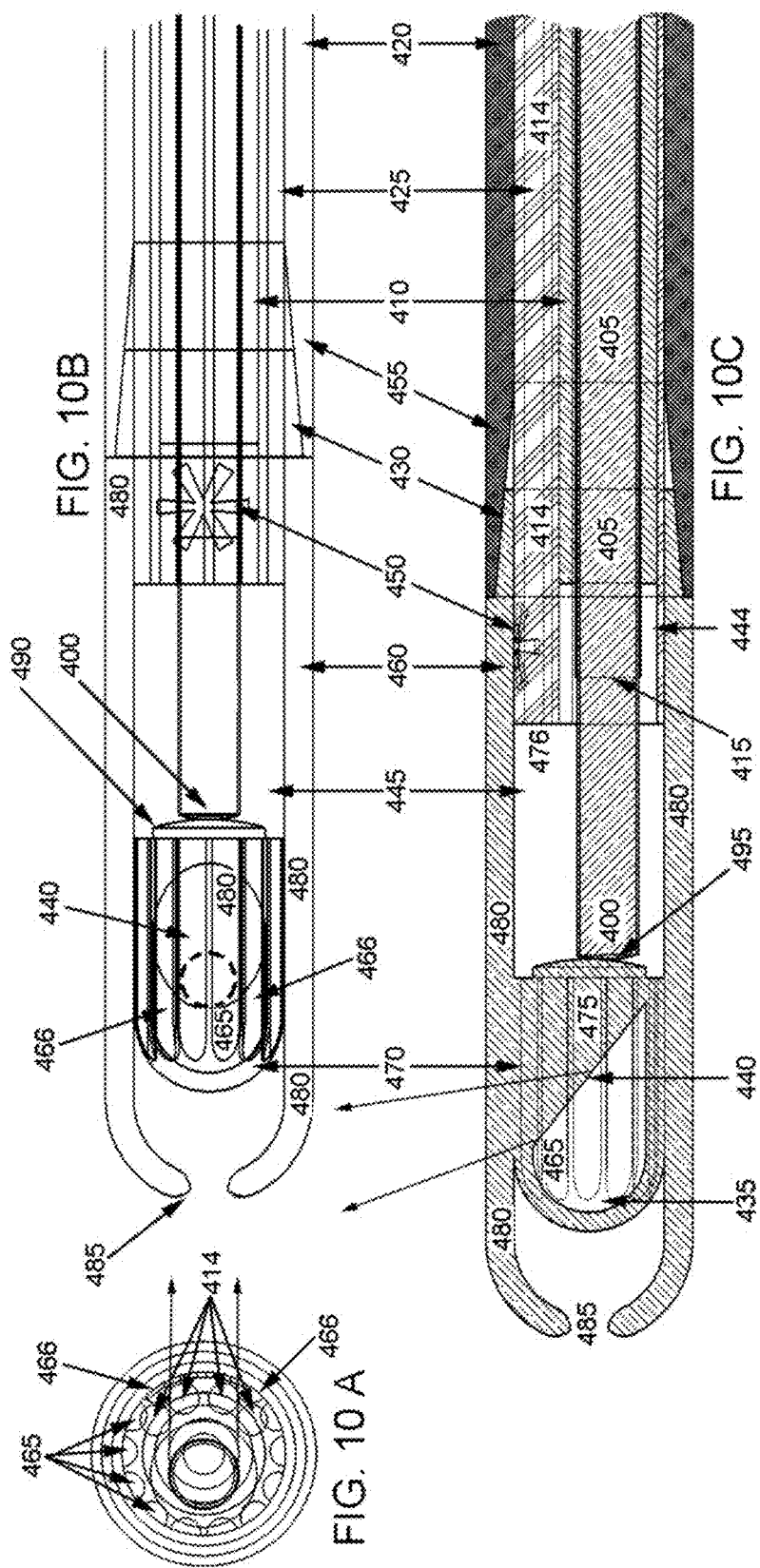

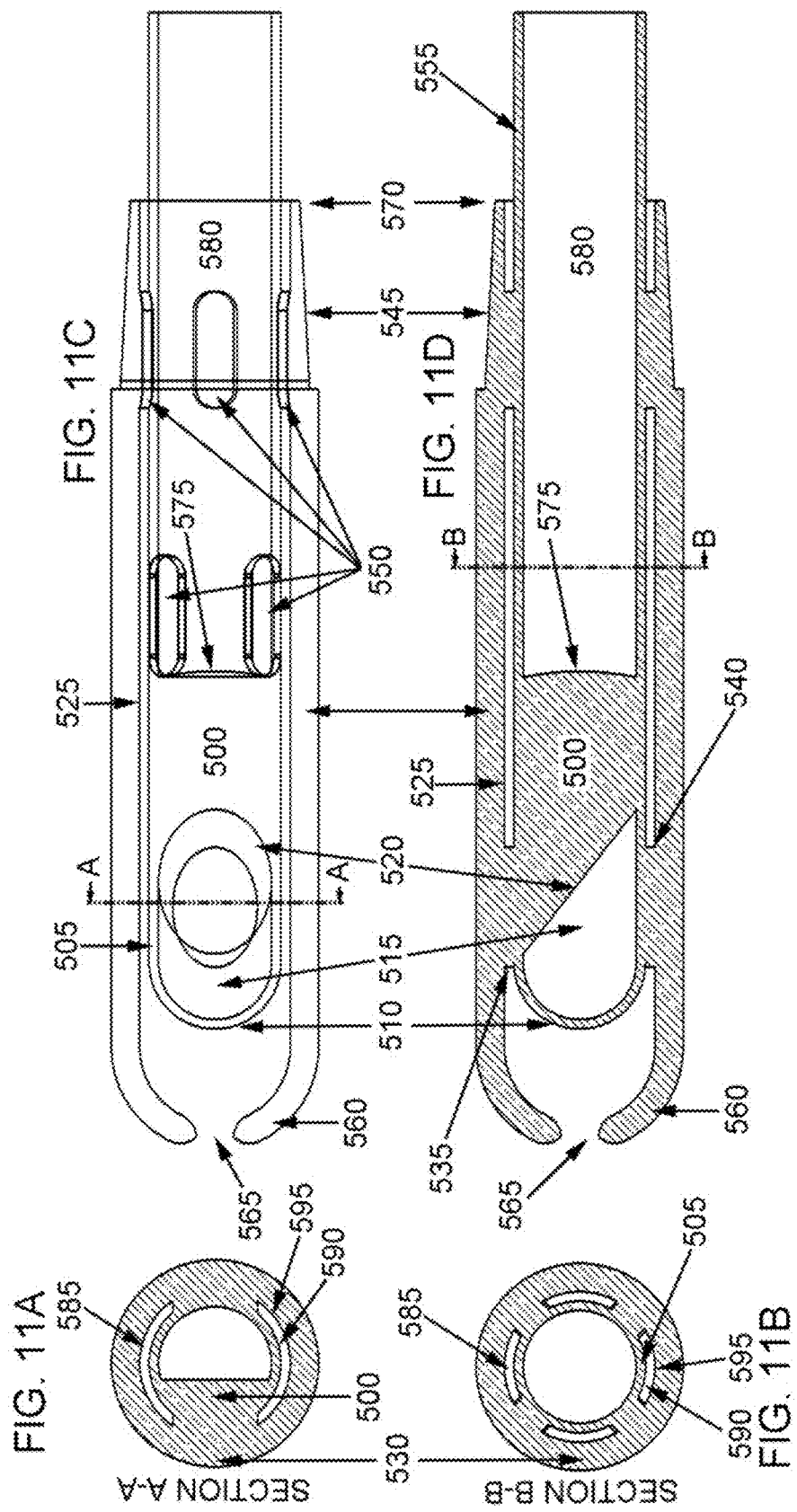

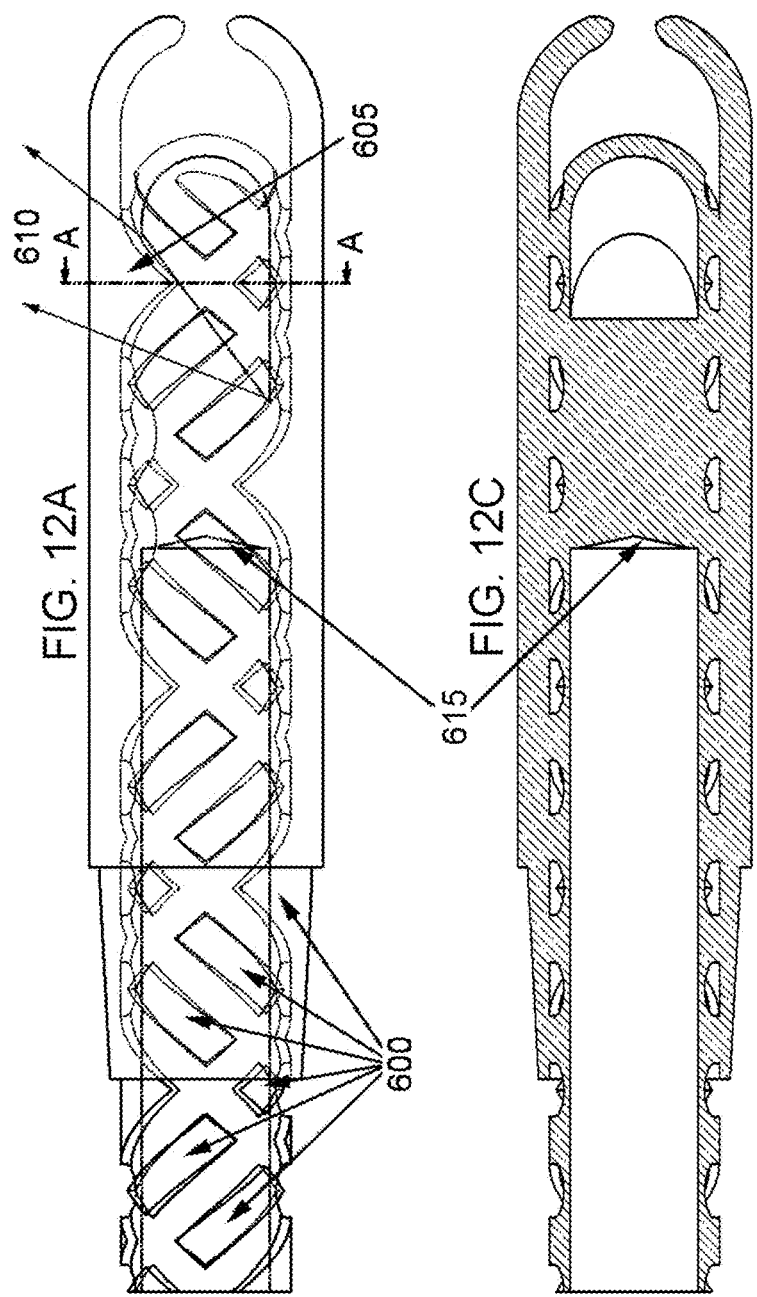

LATERAL DELIVERY DEVICE WITH ACTIVE COOLING

CROSS-REFERENCE TO RELATED APPLICATIONS

This disclosure claims the benefit of priority to U.S. Provisional Patent Application No. 62/387,475, filed Dec. 24, 2015, the entirety of which is incorporated by reference herein.

FIELD OF THE INVENTION

Water cooled, side firing laser surgical fibers are disclosed for use in vaporizing tissues, such as found within enlarged prostate glands, particularly for use at laser wavelengths where water absorbs strongly. While surgical applications are those of principal interest, other applications in spectroscopy and imaging are possible.

BACKGROUND

Continuous wave (CVV) and pulsed infrared lasers, producing radiation within the wavelength range of approximately 1.5 µm to 2.2 µm, are useful for minimally invasive ablation/vaporization of soft tissues. Functionally, this utility is due to the high water content of tissue strongly absorbing infrared radiation in this range; commercially, this utility is due to the availability of relatively low cost, flexible, reliable and biocompatible silica core optical fiber for delivery of these wavelengths. Concentrated and localized heat is produced at the tissue and imposes an upper limit on the average power that may safely be applied without severely damaging the delivery device; even at moderate-average power this heat damages lateral delivery surgical fibers.

Coaxial cooling, where water flows about the fiber circumference at the output, has been used to extend the lifetime and upper power limit of lateral delivery devices, but strong absorption in the near infrared limits the utility of these devices outside shorter wavelengths, e.g., those within the biological window. At longer wavelengths (e.g., 1.5 µm to 2.2 µm), a 'Moses bubble' (a steam bubble) is generated whenever sufficient laser energy encounters water (or aqueous solutions like sterile urological irrigation fluids). When pulsed lasers are used, such as holmium lasers, a distinct popping sound is produced as a steam bubble forms and collapses with each laser pulse. A constant stream of steam bubbles displaces the cooling water in water-cooled side fire fibers leading to thermal damage and the practical exclusion of these fibers at wavelengths in the range where water absorbs strongly.

Generally, gravity-fed (low pressure) coaxial cooling of a side fire fiber greatly improves the fiber useful lifetime (FIG. 6). Prior to these designs, the best side fire fibers on the market survived between 100,000 joules and 250,000 joules before becoming so devitrified and pitted that the output direction and the output spot irradiance became unsafe and ineffective. Damage to the fibers include water intruding into the protective cap via a through-wall perforation (indicated by axial emission), and the cap detaching from the fiber or the fiber simply melting away. Prior to these designs, approximately 15% of all 532 nm laser prostate resection cases required a second fiber to complete surgery and some cases required three fibers (e.g., Laserscope/AMS fiber model 2090 fiber, 80 W or 120 W @ 532 nm). The water-cooled design typically survives 650,000 joules without catastrophic damage even while the 532 nm laser output power has been increased to 180 W.

Variations abound in fiber device tips for surgical applications and the following are directed, primarily, at the side firing devices. This list shows examples that incorporate some aspect of cooling, or potential cooling, of the side fire fiber or tip.

U.S. Pat. No. 5,246,436 (Rowe) describes a fiber device with a metallic and reflective coating on the tip of a conically polished fiber and a void (a hole or port) in the reflective coating permitting light to exit. The tip of the fiber is surrounded by a water channel where the fluidic exit corresponds to the light exit. Rowe teaches (Moses) bubble formation beginning within the emission optical path and within 5 microseconds post laser pulse initiation, followed by bubble expansion with a second laser pulse such that the subsequent pulses pass through the steam bubble to the target tissue.

U.S. Pat. No. 5,409,483 (Campbell, et al.) teaches a side firing fiber device complete with direct visualization of the proximate area about a side fire fiber with the fiber centered in a saline filled balloon. Campbell teaches saline pressure inflating the balloon to compress the targeted tissue to permit deeper penetration of coagulating energy density.

U.S. Pat. No. 5,454,807 (Lennox, et al.) teaches the provision of coaxial coolant flow, gaseous or liquid, for prevention of surface tissue damage for the stated reason of permitting the application of more laser energy to underlying tissues for exogenous chromophore activation in photodynamic therapy (PDT).

U.S. Pat. No. 5,496,309 (Saadat, et al.) discloses fluid flow about a light redirecting prism (that is in communication with the flat tip of an optical fiber) where the prism TIR surface is in contact with the fluid. As such, the prism must be composed of a non-silica material with a refractive index significantly higher than that of the fluid in order to support right angle redirection under the constraints of Snell's law. Fluid flow and laser energy exit a common port.

U.S. Pat. No. 5,672,171 (Andrus, et al.) teaches an axial emitting fiber, housed within a cannula through which saline is flowed to maintain the fiber temperature under approximately 100° C. during use, delivering up to 10 W of 1064 nm (Nd:YAG laser) energy.

U.S. Pat. No. 5,685,824 (Takei) teaches a "prostascope" provisioned with a standard working channel to accept an optical fiber and deliver irrigant to the general surgical field (as does any standard cystoscope) but where a reflector is positioned within a side opening of the working channel for redirecting laser energy laterally with respect to the scope longitudinal axis.

U.S. Pat. No. 6,802,838 (Loeb, et al.) teaches a side firing fiber housed within a nested, dual coaxial lumen device whereby cooling fluid is passed about the side fire fiber within the central lumen, with light exiting a common port with the fluid, and where coolant fluid and debris are evacuated through the second, surrounding lumen.

U.S. Pat. No. 6,953,458 (Loeb) teaches a coaxial coolant channel about an axial fiber where a gas and laser energy exit a common port, where the channel may be angled for access to orthogonally situated tissues, where the gas produces a substantially fluid-free optical path for the laser radiation to reach target tissues.

U.S. Pat. No. 7,359,601 (Loeb) is a continuation-in-part of Loeb '458, teaching adaptations for standard side-firing fibers and teaching suitability of bare, bevel-tipped side fire fibers, operating in irrigation fluid-free space provided by the gas flow.

U.S. Pat. No. 7,492,987 (Yeik, et al.) teaches avoidance of "erosion" of side fire fiber caps that is said to be due to both scatter (or stray or aberrant emissions) laser energy and "back-scattered" laser energy from the tissue itself, with degradation of performance (or loss of laser energy delivery efficiency) from damage to the TIR beveled tip of the optical fiber or capillary in which an optical fiber with the "distal end beveled at an angle of about 30° to 50° is encased in a closed-ended capillary tube for internal reflection of the laser energy, using laser energy of wavelengths of about 300 to 3000 nm". Improved device longevity is taught for fibers that are very similar to those taught by '601, but with the addition of a reflective metal strip or coating within the bore of a needle-like sheathe that acts to form a fluid channel about the glass capsule. An increase in contact vaporization longevity from 86,206 J (3.07 J per pulse, 26 pps, and 18 minutes to failure) to greater than 287,352 J (same settings, one hour and still functioning) is taught to be a result of the addition of a silver metal strip behind and around the glass capsule.

U.S. Pat. No. 7,909,817 (Griffin, et al.) discloses a dual cap side fire fiber where the side fire function is provided within the inner, thin walled cap, and the protective function is performed by a thicker, outer cap, with cooling provided by irrigation fluid flow in the annular space that is formed between the two caps. This technology will not function in the infrared region of interest herein, due to 'Moses bubble' formation within the confined space interfering with coolant fluid flow, but at the 532 nm of the GreenLight XPS™ laser, it is the most widely used side fire fiber to date: American Medical Systems' MoXy™ fiber (AMS is currently a part of Boston Scientific and owns the preceding trademarks).

U.S. Pat. No. 8,529,561 (Griffin, et al.) is a divisional of Griffin '817 describing methods for disruption of laminar flow within the annular, coaxial fluidic conduit.

U.S. Pat. Pub. No. 2014/0074072 (Griffin, et al.) is a continuation-in-part of Griffin '561, teaching rotation of the outer, secondary capsule during surgery.

U.S. Pat. No. 8,858,542 (Peng, et al.) describes a side fire fiber that is cooled within and around the fiber output, with coolant flow exiting a common port with laser radiation and coaxially about the fiber tip.

U.S. Pat. Nos. 8,932,289, 9,005,195 and 9,017,324 (Mayse, et al.) teach cryogenically cooled tissue ablation devices for treatment of chronic obstructive pulmonary disease with various forms of energy, preferably radio frequency energy (but including laser energy) where cryogenic coolant is delivered via a lumen to a balloon, within which or about which resides the energy delivery electrode or presumably an optical fiber or fibers (in the case of ablation by laser energy).

Another tactic for improving the life expectancy of surgical fibers includes coaxial cooling of fiber tips with gas flow. As early as the 1980s, "gas-cooled" Nd:YAG laser compatible fibers were produced for 'open surgery' applications (often non-endoscopic and with no irrigation) such as found in the ear, nose and throat (ENT) specialization, where a circumferential sheathe of gas protects fiber output tips, from accumulation of blood and tissue ejecta. A niche market remains for these fibers even today.

Other rationalizations for passing gases and liquids across fiber surfaces or over tissues appear in the prior art, e.g. cooling tissue in cosmetic and other non-ablative laser procedures to permit more laser interaction with target chromophores before reaching pain or damage thresholds (tattoo ink, spider veins, port wine stains and activation drugs for PDT), where the coolant is provided coaxially to the target (as opposed to the fiber), e.g. U.S. Pat. No. 6,436,094 (Reuter). In endosurgical applications of lasers, much of the cooled fiber prior art is concerned with side firing fibers for laser vaporization of the prostate or axial firing fibers for prostate enucleation.

Relying upon delivered gas to bubble past the irrigation flow within the cystoscope working channel is likely inadequate for providing sufficient gas to displace the irrigant while simultaneously providing adequate irrigation. Surgical interventions can take more than an hour: e.g. for relief of the symptoms of benign prostatic hyperplasia (BPH) where the surgical site is the prostatic urethra, adjacent to the urinary bladder. Were pressures within the urethra to rise sufficient to open the interior sphincter, inflating the bladder, the ureters and ultimately the kidneys, potentially fatal consequences could result due to gas perfusion into the extensive kidney capillary bed. Perfusion into capillaries exposed by the surgery itself could be problematic on its own. While some portion of the optical path may be free of water during some portion of energy delivery events at sheath gas flows compatible with BPH surgery, total displacement of irrigant from the optical path is improbable, and were it possible, the fiber tip would rapidly overheat and melt under modern surgical conditions. In fact, all known commercially available side fire fibers instructions for use caution against firing in air. In-house testing of market available holmium laser compatible side fire fibers demonstrated that the fibers are catastrophically damaged at 20 watts, average power.

SUMMARY OF THE INVENTION

An improved laser surgical device is provided having a proximal end for coupling to the laser energy source and a distal end from which laser energy is emitted. A hollow sheath surrounds the distal portion of the energy delivery conduit for coaxial communication of coolant fluid to the distal terminal tip. In the preferred embodiment a transparent capillary capsule, e.g. fused silica or fused quartz, is equipped with coolant fluid conduits and optical redirection elements whereby the coolant is sequestered from the optical path, permitting operation with lasers producing radiation that may be strongly absorbed by the coolant.

A first embodiment is termination for an optical fiber. This termination can include a tube portion comprising a fluid emission aperture and an optical emission surface; an optical element contained within the tube portion that includes an unbroken light path from an input surface to the optical emission surface, the optical element further including a reflecting surface configured to direct electromagnetic radiation from the input surface to the optical emission surface; and a confined flow passageway for transfer of a fluidic medium through the tube portion to the fluid emission aperture, the confined flow passageway adjacent to the optical element but external to the light path.

A second embodiment is termination for an optical fiber that can include a tube portion comprising an optical emission surface; an optical element contained within the tube portion that includes an unbroken light path from an input surface to the optical emission surface, the optical element further including a reflecting surface configured to laterally redirect electromagnetic radiation from the input surface to the optical emission surface; and a means for preventing pitting of the optical emission surface and disruption of the light path.

A third embodiment is a termination for an optical fiber that includes a tube portion comprising a fluid emission aperture and an optical emission surface; an optical element contained within the tube portion, the optical element including an optical fiber, the optical fiber carrying a reflecting surface as a beveled termination and having an input surface distal from the beveled termination, the reflecting surface configured to direct electromagnetic radiation from the input surface to the optical emission surface, the optical element further including a quartz or silica capsule, the quartz or silica capsule disposed about the beveled termination; and a confined flow passageway for transfer of a fluidic medium through the tube portion to the fluid emission aperture, the confined flow passageway adjacent to the optical element but external to the light path.

A fourth embodiment is a process of prolonging an output quality for a side-fire fiber. This process can include providing a termination for an optical fiber that includes a lateral redirection of a light path from input optical fiber to an output surface; passing a cooling fluid through a confined flow passageway within the termination, wherein a cooling fluid flow path does not intersect the light path; thereby reducing degradation of an output signal.

A fifth embodiment is a laser surgical process that can include providing a termination for an optical fiber that includes a lateral redirection of a light path; cooling the termination by passing a cooling fluid through a confined flow passageway within the termination; and preventing Moses Bubble formation within the termination.

A sixth embodiment is a laser surgical process that can include providing a termination for an optical fiber that includes a lateral redirection of a light path; the termination including a tube portion comprising a fluid emission aperture and an optical emission surface, an optical element contained within the tube portion that includes an unbroken light path from an input surface to the optical emission surface, the optical element further including a reflecting surface configured to direct electromagnetic radiation from the input surface to the optical emission surface, and a confined flow passageway for transfer of a fluidic medium through the tube portion to the fluid emission aperture, the confined flow passageway adjacent to the optical element but external to the light path; and cooling the termination by passing a cooling fluid through a confined flow passageway within the termination.

BRIEF DESCRIPTION OF THE FIGURES

For a more complete understanding of the disclosure, reference should be made to the following detailed description and accompanying drawing figures wherein:

FIG. 3 is a set of photos for comparison of prior art performance: FIG. 3A is the DuoTome SideLite fiber of FIG. 2 and FIG. 3B is the LDD75 of FIG. 4.

FIG. 4 depicts typical perforation damage in a prior art optical fiber where the FIG. 4A top view is a view from the tissue perspective and FIG. 4B is a cross-section side view FIG. 4A.

FIG. 5 is a pair of electron micrographs of the transmissive surface of a used, prior art side fire fiber where FIG. 5A is the transmissive surface and surrounding area of the glass capsule and FIG. 5B is a higher magnification of a portion of FIG. 5A, showing greater detail.

FIG. 6 depicts the prior art where FIG. 6A is a top view from the perspective of the tissue and FIG. 6B is a cross-sectional side view of FIG. 6A.

FIG. 7 illustrates the assembly steps for producing the one-piece transparent side firing capsule of a preferred embodiment of the invention disclosed herein where FIG. 7A is the optical element precursor, FIG. 7B is the optical element with the Total Internal Reflection bevel, FIG. 7C is the optical element with the input lens formed, FIG. 7D is a cross-section of the optical element fused within the inner capillary capsule, FIG. 7E is the inner capillary capsule equipped with machined flats, FIG. 7F is the inner capsule fuse within the outer capsule, FIG. 7G is the completed one-piece side fire capsule and FIG. 7H is a detail showing the fluidic input to the one-piece side fire capsule, shaded.

FIG. 8 provides a top view FIG. 8A (from the tissue perspective) and a cross-sectional side view FIG. 8C of a preferred embodiment of the invention with supplementary cross-sectional views FIG. 8B and FIG. 8D providing views of the cooling channels.

FIG. 9 offers multiple views of a preferred embodiment; two orthogonal views where FIG. 9A is a side view and FIG. 9B is a top view, both with supplementary cross-sections FIG. 9C and FIG. 9D, respectively, illustrating the cooling channels and FIG. 9E is an isometric view.

FIG. 10 provides a top view FIG. 10B and a cross-sectional side view FIG. 10O of a preferred embodiment of the invention with a supplementary and orthogonal cross-section view FIG. 10A for illustration of the cooling channels.

FIG. 11 illustrates an alternative embodiment of the invention in a top view FIG. 110 and cross-sectional views in two orthogonal planes, FIG. 11A and FIG. 11 D, with an additional cross-section FIG. 11B at a second axial location for better illustration of the cooling channels within the one-piece side fire capsule.

FIG. 12 depicts a preferred embodiment having turbulent flow, and shows a side view FIG. 12A and two mutually orthogonal cross-section views FIG. 12B and FIG. 12C for illustration of the cooling channels within the one-piece capsule.

Figure 1:
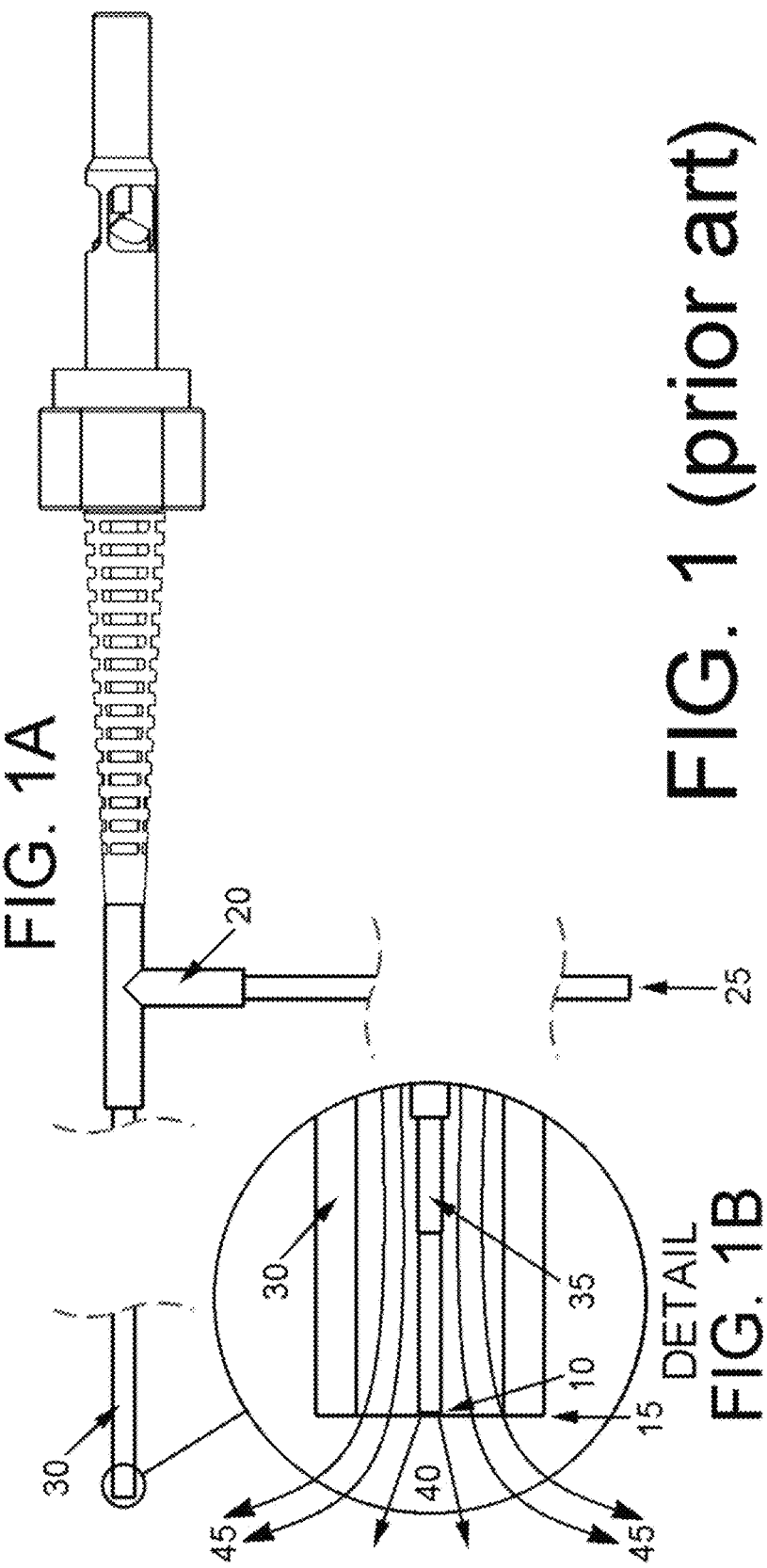
FIG. 1 depicts the prior art of Loeb '458, a gas cloaked axial fiber for surgery FIG. 1A with detail of the output portion FIG. 1B.

While specific embodiments are illustrated in the figures, with the understanding that the disclosure is intended to be illustrative, these embodiments are not intended to limit the invention described and illustrated herein.

DETAILED DESCRIPTION

"Saline" and "water" are used interchangeably herein to mean any physiologically compatible, aqueous irrigation or perfusion fluid that is generally known in the practice of medicine, including Ringer's and simple sugar solutions. "Water" is typically used where water is the element of interest to the discussion, regardless of solutes present and "saline" is used only if salts are used in the solution (typically "normal saline" or 0.9% NaCl w/w) and the presence of the salt is germane. "Proximal" refers to toward the laser and "distal" refers to toward the patient, as has been the consensus convention in the prior art. "Fused quartz", "quartz", "fused silica", "silica" and "glass" are used interchangeably unless otherwise indicated by the prefaces "natural" for fused quartz and "synthetic" for fused silica, reflecting the origin of the raw material used in fabrication and the consequent chemistry of the glass. "Devices" are often referred to as "fibers" in the field and the terms "cap"

and "capsule" may refer to both metal and glass structures. The term "lens" is sometimes used in the field to refer to glass capsules as well. "Irradiance" refers to power per unit area and "radiant intensity" is power per unit solid angle.

Numerous problems have been identified with prior art water-cooled side fire fiber devices including catastrophic failure of devices. Elsewhere, the sources of these problems are identified as deriving from the absorption of laser radiation by saline or water at the laser output or as due to back reflections imparting damage to the delicate, angle-polished fiber tips. For example, the Boston Scientific/AMS' MoXy™ fiber (sold for exclusively for use at 532 nm upon the GreenLight XPS™ (180 watt) laser system and illustrated in FIG. 6), in approved use at 532 nm, has an anecdotally reported failure mode where steam bubbles (produced by induced tissue charring and as sanctioned in the manufacturer's literature for best efficiency) engulf the fiber tip 175, causing flash heating and fracture failure within the highly stressed glass-to-glass fusion of the inner capsule 170 to the fiber cladding 157.

Side fire fibers of all makes and models suffer a common failure mode that has been largely attributed to normal wear and tear in the past. The literature is mostly silent as to a mechanism for the failure and, indeed, many see multiple failure modes within this normal wear and tear rather than a common mechanism: terms describing the failure(s) appearing in FDA's MAUDE (Manufacturer and User Facility Device Experience) database include: spontaneous destruction, axial output, cloudy/foggy cap, charred cap, erosion, corrosion, unintended laser output, laser tip separation, damaged lens, perforation, misfire, overheating. It is a thesis of this disclosure that these failures are largely one in the same.

One data point supporting a common mechanism for disparately reported failures is that thulium lasers producing 2000 nm and holmium lasers producing 2100 nm are more damaging to side fire fibers than 532 nm lasers, and the reason for this difference is generally accepted to be due to subtle, but important differences in how the fibers are position relative to the tissue; 532 nm laser fibers are used in so-called "non-contact vaporization" of tissue where infrared laser fibers are "contact vaporization" devices. (It should be noted that this commonly cited difference in longevity is anecdotal and may well be more myth that fact.) The difference in contact and no-contact vaporization modes of use comes about because the surgical field is irrigated with strongly absorbing saline which favors the infrared fiber being placed in contact with the tissue to avoid excessive energy loss in Moses bubble formation. Water is transparent at 532 nm so the fiber may be held off of the tissue surface with only minor reduction in irradiance.

Some clinicians and investigators have attributed differential longevity of infrared versus visible side fire fibers to the wavelength and pulse nature of holmium lasers themselves, because holmium lasers induce local expansion and implosion on Moses bubbles, where the cavitation damages the glass output capsules. Wth the introduction of CW thulium lasers to the surgical armamentarium that produce similar wavelength to holmium lasers, the sonofragmentation theory has been largely debunked in that side fire fibers are no more reliable on thulium lasers as opposed to holmium lasers.

Most agree that tissue adhesion on the output surface (or transmissive surface) is at least a contributing factor to reducing side fire fiber lifetimes as well as explaining, in part, the different lifetimes for side fire fibers observed for visible (non-contact vaporization) versus infrared (contact vaporization) lasers. In reality, tissue adheres to all side fire fibers regardless of their use in contact or non-contact vaporization, on holmium, thulium, 532 nm, or diode laser consoles. A more likely culprit is reduced cooling by irrigation at the hottest portion of the fiber when the transmissive surface is in contact with tissue. That is, fibers in contact with tissue simply get hotter than fibers that are held a millimeter or two away from tissue.

Technically speaking, all BPH fibers are water-cooled, but that cooling is relatively static. Irrigation is supplied to the urethra (locus of the prostate gland) by way of the cystoscope working channel (aka forceps channel): the same channel that the fiber passes through to access the surgical site. The surgical environment is typically perfused with normal saline, fed by gravity from elevated bags, but the vast majority of scopes are one-way flow. The urethra is filled and the inlet valve is shut. When the surgical field becomes cloudy with blood and tissue fragments, the irrigant is drained and replaced. It is a thesis of this disclosure that such static cooling is inadequate for protecting side fire fibers from overheating in use.

This thesis is supported by observations of average lifetimes for MoXy versus its predecessor, the model 2090 (Laserscope/AMS/Boston Scientific). The model 2090 is still in use today upon lower power 532 nm lasers (80 watt and 120 watt). This basically typical side fire fiber fails to complete surgery in approximately 10% to 15% of cases at 80 watts (532 nm), corresponding to a surgical lifetime of approximately 150,000 J to 250,000 J. Wth the introduction of a 120 watt GreenLight™ laser in 2006, the failure rate remained largely unchanged even with the addition of a multilayer dielectric reflector on the back side of the 2090 fiber. The fact that failures did not increase dramatically may be due to reduced tissue adhesion on this back surface, as will be discussed below.

The need to use a second costly (~$750) disposable fiber for completing surgery 15% of the time is unacceptable to many urological surgeons, so use of the 80 watt and 120 watt lasers has declined precipitously with the introduction of the MoXy, which is not sold for use on the lower power lasers. MoXy is said survive up to 650,000 joules (180 watts, 532 nm) and is capable of treating large glands (>120 grams) with a single fiber (source, AMS brochure). The principal difference between MoXy and the model 2090 is that the MoXy is actively water-cooled.

It is a thesis of this disclosure that active cooling reduces tissue adhesion dramatically, but while prototypes of MoXy made in this laboratory were as depicted in FIG. 6, with an all glass tip, MoXy as produced by AMS/Boston Scientific is also protected by a metal cap about the outer glass capsule, similar to DuoTome. The metal cap prevents tissue from contacting the glass capsule everywhere except at the "window" (transmissive surface).

It is a thesis of this disclosure that "scatter" (output in directions other than the primary beam) that is typically present in side fire fibers at between 5% to 20% of the laser power promotes adhesion of tissues where the scatter exits the capsule because scatter irradiance is below the tissue vaporization threshold. The adhered tissue is charred to carbon over time by the scatter. Carbon strongly absorbs any laser wavelength and the heat that is generated is conducted to the glass capsule. When the temperature of the glass capsule as a whole reaches a threshold, tissue adheres indiscriminately but the additional adhesion is largely a nuisance rather than a contributor to failure. Notably, the fiber capsule need not be in contact with the target tissue to suffer tissue contamination and charring; there are plenty of tissue fragments free floating within the irrigant.

An actively cooled fiber also reduces the load of floating tissue fragments in establishing some level of continuous flow capability instead of the one way flow described above. In order to establish constant flow through the fiber, into the surgical site, equal drainage is required.

MoXy is also highly efficient in its lateral redirection function, presenting very little scatter in the output beam due to the fused cap and water-filled gap 145 in the output optical path (arrows in FIG. 6B). The multilayer dielectric coating on the 120 watt version of the model 2090 fiber blocked back scatter and backscatter is the primary direction of scatter in most glass capped side fire fibers: essentially the reverse of the intended output due to Fresnel reflections within the capsule. It is a thesis of this disclosure that efficient beam steering, that is minimal scatter and minimal distortion of the lateral output beam, reduces tissue adhesion in glass capped side fire fibers and therefore prolongs their useful lifetime.

Figure 2:
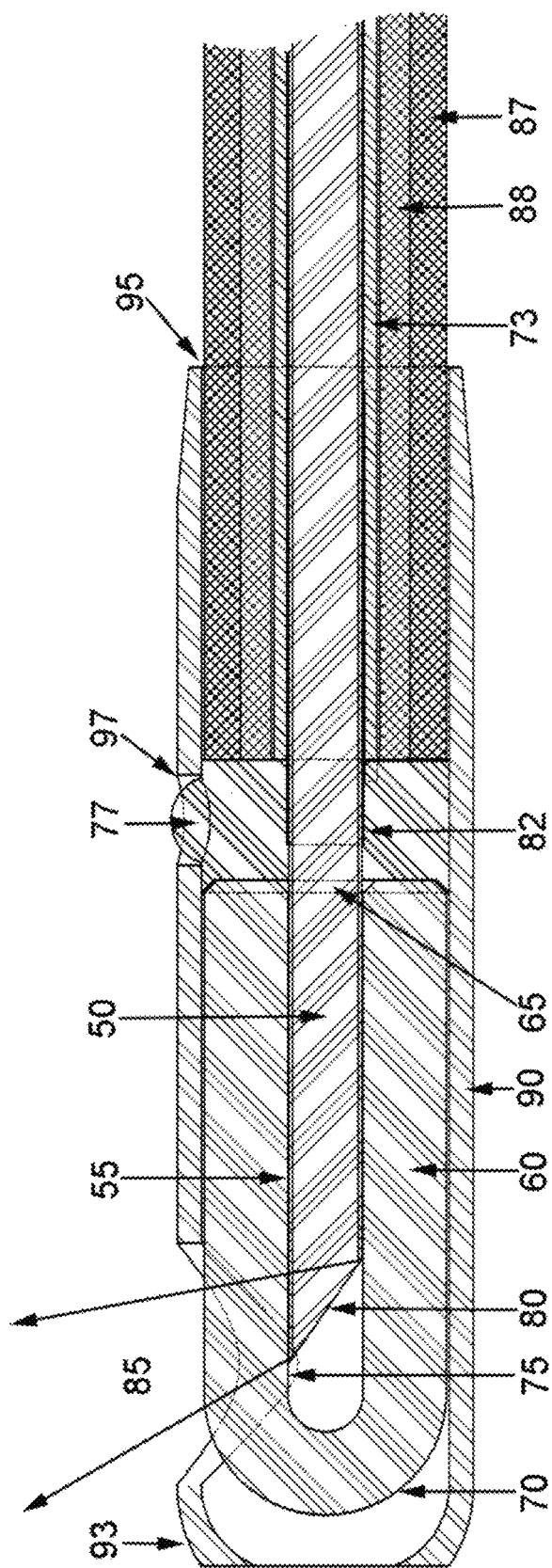
FIG. 2 depicts a prior art optical fiber that is not actively cooled: Lumenis' DuoTome™ SideLite™.

Metal capped fibers like DuoTome FIG. 2 reduce tissue adhesion due to sub-vaporization threshold scatter completely but they do so by treating the symptom rather than the cause. FIG. 2 depicts a silica core 50, fluorine-doped silica clad 55 optical fiber disposed within a fused silica glass capsule 60, open at one end 65 to accept the bare glass fiber and closed at the opposite end 70. The fiber cladding 55 is fused to the capsule bore 75 about a beveled terminus 80 intended to greatly reduce Fresnel and total internal reflections within the optical path 85. The glass capsule 60 is disposed within a stainless steel sleeve 90, open on one end 95 to receive the capsule, the fiber coating (typically a fluoroacrylate) 82, the fiber buffer 73 (typically a polyamide or polyamide/imide such as Nylon® or fluoropolymer polymer such as ETFE), and surrounding semi-rigid tubes 87 and 88 (typically polyether ether ketone aka PEEK), and partially closed on the opposite end 93 to provide a fillet for smooth passage within cystoscope working channels. The steel sleeve 90 is further equipped with a small hole 97 in one side through which an adhesive 77 is added to fill voids and form seals.

DuoTome performs better than any other side fire fiber for infrared lasers, yet like the model 2090 fiber, it does not perform well enough to retain high performance throughout many surgical sessions, even for relatively small prostate glands often failing catastrophically before completing surgery on moderately sized glands (>50 grams). More insidiously, as the fiber performance degrades with use, the surgical advantages of laser vaporization over thermal melting diminish, as the character of the energy applied shifts closer to thermal methods (e.g. electrocautery, microwave). More tissue is coagulated rather than vaporized and the fresh fiber precision in application of the energy is lost. DuoTome, however, is not particularly precise in application of energy even when the fiber is fresh (FIG. 3A) owing to distortions of the TIR bevel face that result from fusion of the relatively thick walled caps 60 to the relatively thin bevel-tipped fiber 80, particularly at the tip of the bevel face.

One advantage DuoTome does have over its infrared side fire fiber competition is the shielding of the bulk of the glass capsule 60 from damage and from tissue adhesion through the use of a stainless steel sleeve 90. Contrary to the failure mechanism taught in prior art '987, it is a thesis of this disclosure that side fire failure is not initiated by reflected laser energy damaging the bevel tip 80, or by imperfect bevel tips, but comes as an indirect result of the absorption of laser energy emitted randomly by poorly designed side fire fibers. Tissue adhesion itself is promoted by the unorganized stray energy, providing illumination of portions of glass capsules with irradiances below the vaporization threshold. First and foremost, failure does not begin inside the fiber capsule: it starts on the outside surfaces, in particular adjacent the transmissive surface, and progresses inward toward the center of the transmitted beam and into the glass capsule wall.

FIG. 5 is two electron micrographs of the transmissive surface of a used side fire fiber (model 2090) showing typical "wear and tear" after normal use in BPH surgery. The large arrow points to the distal terminus of the capsule, roughly 3 mm distant. The cap is approximately 1.8 mm in diameter (wide), for reference. The original, smooth glass surface of the glass capsule 1 is partially visible in FIG. 5A. A remnant of charred tissue 6 is darker in color than the rough material 2, 4, 5 and 7 contaminating the transmissive surface of the capsule. (The rough material appears opaque white in light microscopy.) The elliptical beam profile of the output 2 is bordered by a raised row 4 on the transmissive surface where the irradiance of the output beam falls below the vaporization threshold.

The output beam is elliptical for side fire fibers based upon total internal reflection from beveled surfaces because Snell's law dictates that the critical angle is less than 45 degrees with respect to the fiber longitudinal axis: in the case of the model 2090, the beam exit is centered on 74 degrees (see FIG. 3B). Laser energy is angled distal to the beam exit point, e.g. arrows defining output in FIG. 2, FIG. 6B, FIGS. 8C, 10C and 12A, giving rise to greater heating and tissue adhesion at site 7, the area magnified for examination of the morphology of the distorted surface in FIG. 5B. These features are typically seen with any used side fire fiber.

Myriad myths, misconceptions and false beliefs regarding laser surgery with optical fibers have withstood repeated efforts at debunking throughout the last three decades or so. For example, there is a persistent misconception that the surgical effect of a holmium laser is indirect, with the laser creating a plasma bubble and the plasma bubble exerting the tissue effect. Even surgical experts, among those who concede that at least some of the holmium laser pulse has direct tissue vaporization effect, cling to a photomechanical or sonofragmentation effect of vapor bubble formation and implosion "tearing the tissue apart". As with many misconceptions, this false belief is likely due to holmium laser sales personnel who feel compelled to defend holmium laser efficiency against their 532 nm and diode laser rivals' claims that holmium (and thulium) laser "waste power" due to the Moses effect. Reality is simple; infrared lasers interact with water. Water is vaporized to steam and the latent heat of vaporization for water is huge, therefore significant amounts of infrared laser energy are consumed in vaporizing water. Other misconceptions involve the causes and mechanisms of failure modes and some of these misconceptions have influenced prior art side fire fiber designs.

Prior art water-cooled side fire fibers have uniformly argued for the coolant exiting a common port with the lateral emission, where constructs for accomplishing the common port design necessarily elongate the optical path from the fiber emission surface (aka the transmitting surface or transmissive surface) to the target tissue, thereby increasing the volume of water that must be vaporized by the energy in passage. Notably, no prior art, actively cooled infrared side fire fiber has had broad commercial success. The most successful side fire fiber design for holmium laser ablation of the prostate (HoLAP) is not actively cooled—the DuoTome™ SideLite™ fiber (Lumenis, Israel) is depicted in FIG. 2—and no side fire fiber for infrared laser BPH surgery marketed today is actively cooled.

An example of a currently marketed side fire fiber that has won a modest following (for low power holmium laser applications, not BPH) is the VaporMAX™ by Trimedyne: the subject of prior art '987. While '987 properly teaches that overheating is a fundamental problem for side fire fibers and recognizes that efficiency (as defined by laser energy exiting the fiber in the proper direction) is important to reducing internal heating, '987 also incorrectly teaches that degradation proceeds within the protective cap, specifically that " . . . back-scattered laser energy from the target tissue can erode the buffer coating and cladding of the optical fiber and the optical fiber itself, causing laser energy to be emitted in aberrant directions . . . "

This laboratory's studies over the past 25 years support a clear relationship between fiber longevity and initial fiber efficiency: the greater the portion of laser energy that actually performs surgery—that is the more energy that is redirected to the target tissue without distortion or scatter—the more delayed the onset of performance degradation. Nothing resembling the internal damage to the fiber as taught by '987 has ever been observed even at the end of the failure progression, let alone at the onset of failure. In contrast, as shown in FIG. 5, damage starts on the transmissive surface of the fiber.

Side fire fibers that have been used but briefly to vaporize small glands often appear unscathed to the naked eye, but upon magnification and proper lighting, what some describe as scaling or cloudiness is apparent, similar to that at 8 in FIG. 5A but located in the ellipse that defined the beam diameter, centered on 2, and is most dense in the row 4 that surrounds the elliptical output surface. This is the onset of degradation, and once it has begun it progresses relatively linearly with joules passed until the transmissive surface is adversely affected enough to markedly diminish the quality of the exit beam (as defined by a relatively uniform and sharp edged spot when projected) with some laser energy reflecting back into the capsule, a point typically marked by haziness or crazing on or about the transmissive surface 2. When the transmissive surface for the output beam is damaged, the device scatters energy at lower irradiance and in useless directions that was previously delivered to the target tissue. If the fiber was initially very efficient, little to no laser energy contributed to heating the cap, but as damage invades the transmissive surface the resultant scattered energy produces promotes tissue adhesion wherever it exits the capsule, even where the fiber is used without contacting the target tissue itself. The tissue begins to 'cook', or carbonize: slower in areas of diffuse energy leakage and faster in areas where leakage is more concentrated. As internal heating worsens, so does the erosion of the transmissive surface, because this damage is devitrification, a process favored at elevated temperatures in fused silica.

Fused silica is a super-cooled liquid, at least in the view of thermodynamic equilibria, in that the lower energy forms of silica that are naturally occurring are all crystalline. The crystalline structure is the thermodynamically preferred state of silica; it is only the high viscosity of the super-cooled liquid state that prevents the structural rearrangement necessary to revert to crystalline form. When making fused silica, it is critical that cooling is rapid enough, and that the melt viscosity is high enough, such that the atoms cannot arrange themselves into an ordered state and the amorphous "glassy state" is frozen in. Devitrification is a thermodynamically favorable rearrangement that is aided by intercalation of alkali metal cations, chloride and other halogen anions, and the presence of water (hydroxide, hydronium, etc.) . . . all of which are present in most sterile irrigation fluids used along with side fire fibers.

Alkali metal (and to a lesser degree, alkaline earth) cations absorb and intercalate within the amorphous (fused) silica, lowering the surface viscosity of the glass. This absorption, as well as lower viscosity itself, is kinetically favored as temperature and pressure rises, in enhanced by existing surface flaws, water (particularly hydronium ions) and halide anions, e.g. chloride. If the viscosity is lowered enough, for long enough, the disordered atoms rearrange into high cristobalite (crystalline silica). In short, the surgical environment of laser lithotripsy fibers is the perfect environment for devitrification. As temperatures rise in the fiber tip, devitrification rates increases exponentially.

High cristobalite is difficult to see within the surgical field because its density is very close to that of fused silica, at the moderate temperatures within the surgical fiber micro-environment, but during pauses in active lasing, where the fiber capsule cools below 275° C., high cristobalite rearranges from the cubic to the tetragonal crystal structure with a concomitant reduction in density. This density change results in visible spalling on the glass surface. The tetragonal crystal structure is birefringent so it appears white on clear, dry fused silica (as do fingerprints on a fused quartz halogen light bulb envelope) and on the protective caps of used side fire surgical fibers.

Adhered tissue also contains NaCl, sodium cations and chloride anions, both of which intercalate within the amorphous silica network of the device's glass capsule, reducing the viscosity of the glass at the glass surface. The entire surgical site is typically flooded with 0.9% saline (NaCl in $H_2O$, w/w) which serves to replenish the ions lost to intercalation. Like bacon in a frying pan, the adhered tissue chars, beginning with sub-nanoscale carbon center formation (or 'carbon seeds'). As these carbon seeds grow to nanoscale diameters they scatter more and more energy by the Raleigh model and, when diameters reach approximately 10% of the laser wavelengths, Mie scatter contributes to the chaos. The carbon particles absorb laser energy very strongly, regardless of the wavelength, and dissipate the absorbed photonic energy as heat into the saline surgical irrigation fluid and into the fiber device itself. Heated saline promotes additional devitrification as does the rising temperature of the glass. More scatter promotes more tissue to adhere, which promotes more scatter.

This model is known as "the Devitrification (Failure) Cascade" in our laboratory, and we have identified tissue adhesion as the initiator of failure. More precisely, stray energy initiates fiber failure by promoting tissue adhesion and that energy can be in the form of laser scatter (due to poor fiber design, assembly defect, or damage), Mie and Raleigh scatter (from tissue or irrigation media), or heat (conducted by steam, charred target tissue or accessory fiber components), etc. Prostate tissue has an average refractive index that is just a bit higher than water such that little reflection occurs.

Some of DuoTome and VaporMAX (and even MoXy) longevity is attributable to the thermal conductivity of the metal sleeve (about the glass capsule). The steel sleeve's shielding the glass capsule from direct tissue adhesion is definitely a contributing factor to longevity, but the metal cap may also have negative consequences. Heat conducted away from the transmissive surface of the capsule has to go somewhere and that somewhere is typically occupied by heat labile components of the fiber: polymer coatings, buffer (jacket) and adhesives.

Specifically in the case of VaporMax, the glass capsule is relatively short at just over 7 mm where the metal sleeve is quite long at about 46 cm. The metal cap is actually a separate component made of silver metal that is bonded to the 46 cm steel shaft. Silver has high thermal conductivity and is highly reflective at holmium laser wavelengths; the enhanced lifetime of VaporMAX over its predecessors is most likely due to efficient conduction of heat away from the glass capsule rather than protecting the fiber tip from damage by reflected laser energy as taught in '987.

The superior longevity and failure mode of a new side fire fiber (called LDD75 internally), U.S. Pat. No. 9,323,005 (Griffin), which is incorporated in its entirety herein by reference, supports the theses presented above. In the most basic embodiment of the LDD75 as taught in '005, a one-piece optical component (glass capsule) for lateral redirection of electromagnetic radiation that is coupled to an optical fiber similar to that used in manufacturing DuoTome and VaporMAX. The new device is capable of delivering twice the laser power of the DuoTome maximum rated power rating and survived to complete BPH surgery with thulium and infrared diode lasers in 96% of trials. LDD75 has no protective metal sleeve over the glass capsule, but it does have very high beam quality for the lateral emission. FIG. 3 presents projected beams from a typical DuoTome (FIG. 3A) and a typical LDD75 (FIG. 3B).

FIG. 4 depicts the damage to a LDD75 fiber that is typically observed following completion of a typical prostate vaporization surgery and is consistent with damage observed for prior art devices including LDD75, model 2090 and DuoTome. FIG. 4A is a depiction of the appearance from the perspective of the tissue where 4B is a cross-section taken through the center of 4A. There is absolutely no damage to the bevel 104 or the bevel tip 100, the fiber coating 106, the fiber cladding, 108 or the fiber core 112 as would be expected for the model taught in '987. Instead, the cap 130 is visibly pitted 105. The pit 105 surface appears frosted under moderate magnification. What appear to be cristobalite lepispheres are revealed by electron microscopy (as in FIG. 5B) indicating that the pit is likely the result of repeated devitrification, sloughing cycles as taught in the Devitrification Failure Cascade, described above. The pit 105 is approximately conical, with a rounded apex 110 and filleted base 115 or edge. Additional devitrification is observed radially from the central axis of the pit, becoming more diffuse with distance similar to that seem in the electron micrograph of FIG. 5A. Also similar to 6 in FIG. 5A, dark brown and black specks of charred tissue are observed about much of the circumference of the pit, beginning at the edge of the pit base fillet 120 approximately to the extent indicated by the broken circle 125.

Pitting of the cap is undesirable for two principal reasons; the laser beam exit is aligned with the axis of the pit so the emission is scattered by pitting and, should the pit be permitted to bore-through to the vacuum pocket 135, saline would rush in and the fiber would fire axially. These so-called 'bore-through' failures do occur in surgery but the consequences are typically less traumatic for infrared lasers than for those operating within the biological window, where stray axial emissions may damage the bladder neck or perforate the bladder.

Further evidence supporting the Devitrification Failure Cascade model for side fire fiber failure comes the prior art MoXy side fire fiber, as described in U.S. Pat. Nos. 7,909, 817 and 8,529,561 (Griffin, et al.) and depicted in FIG. 6. MoXy starts off very similar to a fused output side fire fiber where a fiber, having a terminal section 150 that is stripped of the two fluoropolymer coatings (thin coating 155 and buffer 160), is equipped with an angled polish or bevel 165 for total internal reflection (TIR) of the laser energy. A thin-walled silica capsule, one end closed like a tiny test tube 170, is fused about the bare fiber 150 silica cladding 157. This relatively fragile side fire fiber is then positioned in the center of a larger silica capsule 175 that is not completely closed on the end 140 where the outer diameter of the fragile side fire fiber 180 is sufficiently smaller than the bore 185 of the larger capsule 175 to permit water to flow (arrows in FIG. 6A) within the annulus formed by the outer diameter of the inner side fire fiber cap 180, contained by the bore 185.

A semi-rigid tube or cannula 190 with a bore 195 sufficiently larger than the fiber buffer outer diameter 160 is positioned about the fiber and is mated 195 to the proximal end of the larger cap 175 and sealed with adhesive, forming an annular channel for communication of water (arrows in FIG. 6A) through the annular space between the inner cap's outer diameter 180 and the inner diameter of the larger cap 175, to exit through the opening 140 in the end of the larger cap 175.

The thin layer of water at 145, within the optical path, renders MoXy useless for infrared laser surgery, because water strongly absorbs infrared wavelengths. Pulsed infrared lasers such as holmium lasers (2100 nm) vaporize the water layer 145 with each pulse and this cycling of vapor bubble formation and collapse interferes with or even reverses the coolant flow (under gravity feed as in the practice in surgery). In experiments within our laboratory, the position or size of the opening 140 was immaterial to the observation of this phenomenon; even sharing an exit port with the laser output saw water pumped from the surgical site to a reservoir situated one meter above the output tip. In that the surgical site is highly contaminated with floating tissue fragments, pumping in the reverse direction would introduce this detritus to the beam path within the cap annulus, hastening failure.

For continuous output infrared lasers, such as thulium fiber lasers (2000 nm), the water flow is less completely disrupted by a vapor bubble within the cooling channel but the extend of disruption renders the higher cost, water-cooled side fire fibers no better than more standard fibers like DuoTome. Adding a water exit port to coincide with the laser emission, acting in concert with the axial port 140 of MoXy, appears to reposition the Moses bubble enough outside of the fluidic channel to permit some flow, but doing so continues to establish a pathway for contaminated flow from the surgical site to within the side fire cap. Accordingly, the art disclosed herein concentrates upon structures that exclude water from the optical path within the side fire fiber.

Challenges for producing a water-cooled fiber for use at wavelengths where water strongly absorbs the laser radiation are related to the necessary provision of cooling very close to the optical path, particularly at or near the transmitting surface or output surface of the device, without intersecting the optical path with the coolant. Coolant must also be excluded from the air (or vacuum) chamber disposed adjacent to the TIR bevel for maintenance of the total internal reflection at the TIR surface and, in the case of more advance optical designs such as taught in U.S. Pat. Nos. 9,323,005 and 9,488,782 (the disclosures of which are incorporated herein in their entirety), where the lateral redirection function is provide entirely within one-piece side fire caps, coolant must be excluded from the optical path between the transmitting fiber and the cap input surface, e.g. 114 in FIG. 4.

Figure 13:
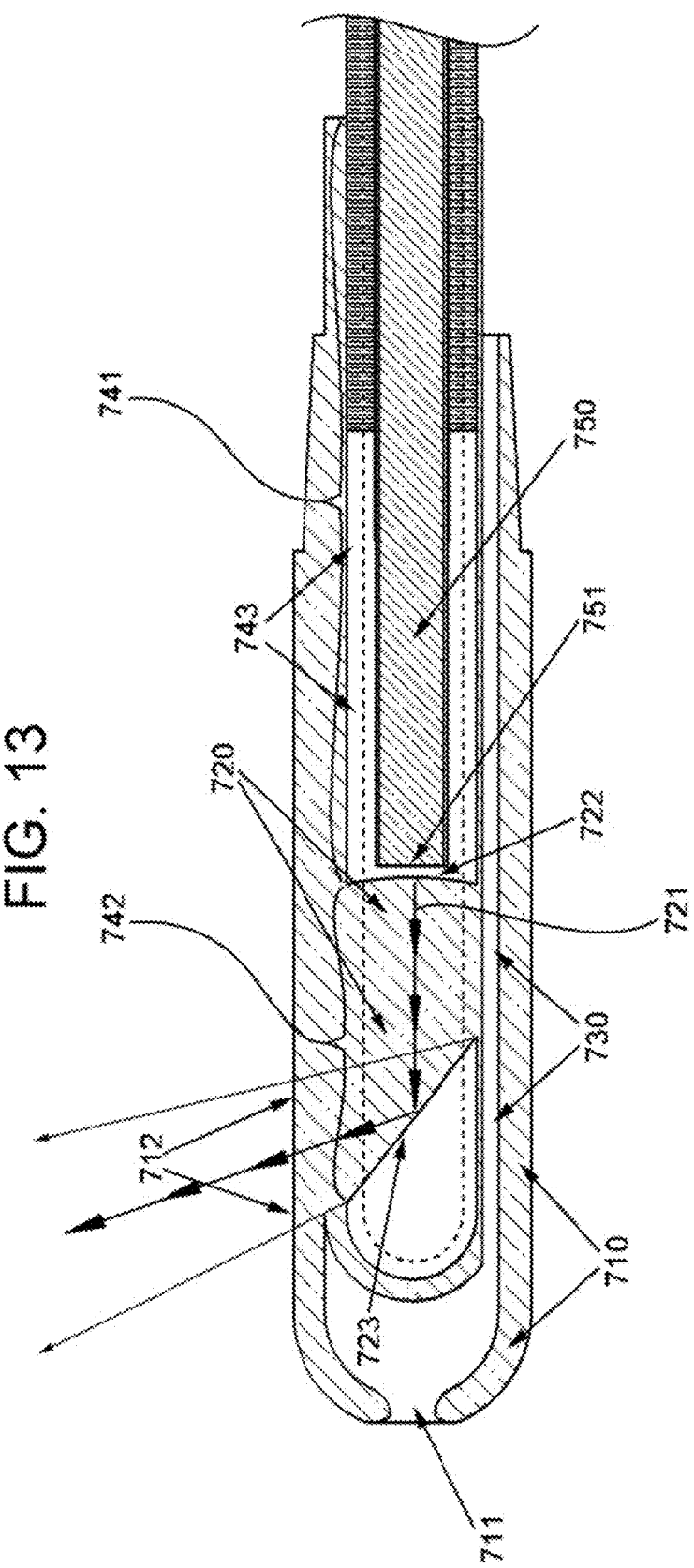
FIG. 13 depicts a side view of one embodiment of the invention.

One solution is an optical fiber termination that includes both redirection of the optical path and active cooling. In one embodiment and in reference to the number in FIG. 13, the termination can include a tube portion 710 comprising a fluid emission aperture 711 and an optical emission surface 712; an optical element 720 contained within the tube portion that includes an unbroken light path 710 from an input surface 722 to the optical emission surface, the optical element further including a reflecting surface 723 configured to direct electromagnetic radiation from the input surface to the optical emission surface; and a confined flow passageway 730 for transfer of a fluidic medium through the tube portion to the fluid emission aperture, the confined flow passageway adjacent to the optical element but external to the light path. Preferably, the reflecting surface is external to the confined flow passageway. As used herein, an unbroken light path means a section of an optical network or pathway in which light travels without being modified by passing through an interface.

In one instance, the termination includes a plurality of confined flow passageways which do not intersect the light path. In one example, these confined flow passageways include helical grooves carried on an external surface of the optical element.

Preferably, the termination includes an optical element has a one-piece construction consisting of fused quartz and/or fused silica. In one instance, the optical element can include a guide section 742 and an open-end section 741. The open-end section and the guide section divided by the input surface. The open-end section including a bore 743 which terminates at the input surface. The open-end section shaped to receive a fiber optic cable; and where the guide section including at least a portion of the unbroken light path. In a preferable instance, the optical element is fused to an internal surface of the tube portion. In this instance, at least a portion of the confined flow passageway can be defined as a volume between the optical element and the internal surface of the tube portion. Another instance includes an optical fiber 750 affixed to the optical element; the optical fiber having an output surface 751 adjacent to the input surface of the optical element.

In another preferable instance, the tube portion and the optical element are a one piece construction consisting of fused quartz and/or fused silica. That is, the tube portion and the optical element are or consist of a fused quartz or silica object. Notably, quartz and silica can be assembled from different parts, joined, and fused to yield a single final object.

In still another instance, the optical element includes an optical fiber, the optical fiber carrying the reflecting surface as a beveled termination and having an input surface distal from the beveled termination, the optical element further including a quartz or silica capsule, the silica capsule disposed about the beveled termination. Preferably, the silica capsule is fused to an internal surface of the tube portion. In one example, an optical pathway extends within the optical fiber from an optical fiber input to an optical fiber output, from the optical fiber output to the input surface, and includes the unbroken light path of the optical element. Preferably, this optical pathway is external to the confined flow passageway.

The formation and details of embodiment can be shown by reference to the accompanying figures; for example, FIG. 7 depicts a method of assembling a one-piece optical element for a preferred embodiment of a water-cooled infrared side fire fiber that solves the problems with existing water-cooled side fire fibers, providing fluidic cooling of side fire fibers for infrared lasers while concomitantly improving upon lateral redirection efficiency and minimizing losses to Moses bubble formation. With somewhat improved lateral redirection efficiency with respect to MoXy, the embodiment need not be restricted to use with infrared lasers: laser surgery at wavelengths operating within the biological window also benefit from the water cooling and improved efficiency of the disclosed invention.

A reflecting bevel 200 is polished at the traditional 35° to 40° off the longitudinal axis of a cylindrical solid blank FIG. 7A of fused quartz or fused silica approximately 2 mm to 4 mm long, yielding FIG. 7B. The opposing end of the cylinder is formed into a lens 205 with a positive or negative curvature FIG. 7C, or cone (convex lens illustrated). A relatively thin wall silica or quartz tube 210 is disposed about the shaped cylindrical solid FIG. 7C and is sealed 215 at the bevel end as depicted in FIG. 7D. Flats are machined at two or three orthogonal sides 220 of the tube leaving the transmitting surface 225 at the original curvature and resulting in FIG. 7E. A heavier wall and larger hollow cylinder 230 of quartz or silica, where the bore 235 of the larger cylinder is very slightly larger than the outer original diameter 240 of the relatively thin walled tube 210, is disposed about the construct of FIG. 7E and the bore 235 is fused 245 to the, remnants of the original diameter 240 of FIG. 7E. FIG. 7E is positioned within the larger cylinder such that a millimeter or two 250 extends beyond the larger tube 230 at the distal end, and a millimeter or two of the larger tube extends beyond the sealed end 215 of the construct in FIG. 7E, permitting formation of a test tube bottom 255, but leaving a hole, or port, 260 rather than a full seal, such that two or three "D" shaped cross-section channels 275 (two of three labeled) are formed producing the construct in FIG. 7F. An outer diameter step 265 and chamfer 270 are formed on the distal end of the larger cylinder 230 yielding FIG. 7G. FIG. 7H illustrates the "D" shape of the distal openings (darkened) of the three resulting channels 275.

FIG. 8 illustrates the functional terminus of the fiber optic device produced from the one piece cap described above (FIG. 7) where FIG. 8A is view from the perspective of the tissue (top view), showing fluid flow (arrows) from the proximal (reservoir) end 285, through the one-piece glass capsule 288 and out the distal port 290. FIG. 8B is a cross-section through the capsule showing the three "D" shaped channels 280 that result from fusion of the machined inner capillary capsule (FIG. 7E) within the bore of the outer capsule 288. FIG. 8C is a cross-section along the longitudinal axis of the device, and 8D is an orthogonal cross-section to FIG. 8C, showing the three "D" shaped channels 280, for aid in viewer orientation. Specifically, a semi-rigid tube or cannula 295 is disposed about the stepped and chamfered 278 (and 265 and 270 in FIG. 7G, respectively,) capsule of the one-piece side firing capsule and sealed thereto, preferably by adhesive. An prepared transmitting optical fiber end 283 (stripped of polymers 299 and polished 284) is disposed within the bore 292 of the cannula 295 and affixed (sealed, preferably with adhesive) in the bore 287 of the inner capsule, with capsule flat sides (220 FIG. 7E) with a portion extending into the cannula 281 (250 in FIG. 7F) with adhesive fixing the nylon buffer 291 within the inner capsule bore 287 to form the fluidic channels for communication between the proximal reservoir, within the bore 292 of the cannula 295 (about the fiber buffer 291) and into the "D" cross-section channels 280 to exit via the distal port 290 into the irrigated surgical field 277. The adhesive seal between the nylon buffer 291 and inner capsule bore 287 must exclude coolant from the space about the bare fiber 283, particularly the gap between the polished fiber face 284 and the input lens surface of the optical element (205 in FIGS. 7C, 7D and 7E)

The optical output path (arrows in FIG. 8C) is contiguous with the input lens surface (205 in FIGS. 7C, 7D and 7E) such that there are no undesirable internal reflections caused by refractive index transitions and no water for Moses bubble formation, yet the output area (bounded by the arrows in FIG. 8C) is surrounded by coolant flow to prevent overheating. Coolant is supplied to the annular fluidic channel within the cannula bore (about the fiber buffer) by a standard T or Y junction, proximal to the cystoscope entry length of the working end of the fiber optic device, as is well known in the art and illustrated in FIG. 1A FIG. 9 illustrates an alternative embodiment of the invention that is produced directly upon an optical fiber, rather than as a one-piece optical element for lateral redirection. A substantial advantage of one-piece cap construction, as opposed to fusion of protective caps and other elements directly to the optical fiber, is that the one-piece construction contains only fused silica or fused quartz or a combination of the two and, as such, internal stresses that are induced in manufacturing may be relieved through annealing—particularly those stressed that are due to spot heating for fusion, where temperature differences may differ by approximately 2000° C. within one millimeter during processing. Annealing in impossible prior to assembly where polymer components are present, as in this embodiment. While the substantial advantage of pre-assembly annealing is lost in embodiments such as depicted in FIG. 9, the water cooling attributes of the embodiment minimize the severity of thermal cycling that the device is exposed to in surgical use, reducing the risks of fracture at stress concentrations within the device. Such fractures do remain a primary failure mode in direct-to-fiber-fusion devices, such as the prior art illustrated in FIG. 6. Anecdotal reports from past MoXy™ sales and support personnel describe fractures of the inner capsule (157 in FIG. 6B) in GreenLight laser BPH cases where stream bubbles rising from the tissue briefly surround the lateral redirection tip.

In FIG. 9, a transmitting optical fiber 380 is prepared by removing a portion of the buffer coating 300 and the thin fluoropolymer coating 305 from one terminus, leaving bare glass cladding 310. An angled reflective face 320 is polished onto the fiber tip and a thin walled silica tube 315 is disposed about the bare fiber, fused 325 about the fiber cladding 310 and sealed 330 at the distal end. The outer diameter of the thin walled tube 315 is machined, forming flats 335 or channels along its entire length and on one or more sides: analogous to the inner capsule of FIG. 7E. A thicker wall and larger tube of quartz or silica 340, where the inner diameter 367 is slightly larger than the original outer diameter of the inner capsule (prior to machining the flats) is disposed about the machined inner capsule and the original outer diameter 388 portions of the inner capsule are fused to the inner diameter of the outer capsule at 345. The outer capsule is incompletely sealed at the distal 34 terminus, leaving an opening or port 350 for communication of fluid between the terminal chamber 390 and the surgical field 399. The proximal terminus of the outer capsule is equipped with a step and chamfer 395 on the outer diameter for mating with a semi-rigid tube or cannula 360. The flared-end cannula 360 is slipped over the buffered fiber 380 and is sealed at the proximal end of the outer cap 395 with adhesive as known in the art.

Fluid is provided to the annular fluid conduit 370 formed between the inner diameter 367 of the cannula 360 and the buffer diameter 300 of the transmitting optical fiber 380 through a T or Y junction as is known in the art and as depicted in FIG. 1A. Fluid within the cannula 360 enters the outer capsule bore 375 and flows about the thin coated fiber 305 and bare fiber 310, then into the "D" shaped channels 385 formed by the fusion of the inner diameter 367 of the outer capsule 340 and the machined flats 335 on the inner capsule, into the terminal chamber 390 and through the distal port 350 to the surgical field 399.

A further embodiment that is not suited for delivery of infrared radiation in wavelengths where water strongly absorbs is illustrated in FIG. 10: a water-cooled adaptation of a truly orthogonal side fire fiber device as described in U.S. patent application Ser. No. 14/958,057, the entirety of which is incorporated herein, by reference. While the embodiment in FIG. 8 may be used within the biological window, design for infrared lasers requires the exclusion of water about the optical fiber terminus 284 (FIG. 8C) least violent vapor explosions be produced as energy is emitted from the fiber tip; permitting water to flow about the fiber tip 400 in FIG. 10 may improve performance somewhat, for wavelengths that do not strongly interact with water, if for no other reason than reduction of Fresnel reflections at the fiber tip 400 and the power input surface (lens 490). A transmitting optical fiber 405 is stripped of its ETFE buffer 410 and fluoroacrylate polymer coating 415 and in this example the fiber terminus 400 is equipped with a convex lens 495. The fiber output lens 495 abuts the input lens 490 of the one-piece lateral redirection element 480, consisting of a shaped cylinder 475 similar to FIG. 7C, a thin walled inner, test tube like capsule 470 similar to 210 in FIG. 7D is equipped with a dozen flutes 465 (for example) as opposed to flats (220 in FIG. 7E) and is fused within a heavier wall and larger outer capsule 460. The proximal end 430 of the outer capsule 460 portion of the one-piece optical element 480 is equipped with a stepped chamfer 430 for mating to the outer cannula 420 at a complementary internal chamfer 455: the chamfered portions are affixed with adhesive as is known in the art.

An inner cannula 425 is equipped with a large and eccentric (relative to the longitudinal axis of the cannula) lumen 444 that carries the buffered transmitting fiber 405 and four fluid delivery lumen 414, for example. Coolant fluid (such as water) is provided to the four delivery lumen 414 at the proximal terminus of the inner cannula 425 by a T or Y fitting as is known in the art, and exits the inner cannula at 476, filling the chamber 445 about the bare fiber end 400, then passes around the TIR element 475 through the multiple flutes 465 in the inner capsule 470 wall and out through the distal port 485.

Light delivered by the transmitting fiber tip 400 couples to the lens input 490 on the TIR element 475 and is focused onto the TIR bevel 440 where the refractive index of the hermetic space 435 preserves total internal reflection (TIR). The focused energy reflects at an angle slightly higher than twice the TIR angle (relative to the fiber longitudinal axis) due to the astigmatic distortion of launching into the lens 490 off of center. The reduced divergence within the focal waist permits emission (small arrows in FIG. 100 and dotted circle in FIG. 10B) to skirt the coolant flutes 466 on either side of the optical path.

The next embodiments address infrared (absorbed by water) wavelength designs but, as noted above, infrared designs may be used with wavelengths that are not absorbed by water and the modifications required to connect fluid flow for closer refractive index matching between transmitting fibers and the input surfaces of the water-cooled, single-piece lateral redirecting optical elements depicted will be clearly apparent to those skilled in the art. These embodiments are depicted without the transmitting fibers, fiber positioning or fluid delivery cannulas for clarity in illustration, as some of the fluidic pathways are rather complex. The complexity of the fluidic pathways is not proportional to the difficulty of fabrication, as is illustrated by comparing FIG. 11 versus FIG. 12: FIG. 11 is challenging to produce where FIG. 12 is relatively simple.

FIG. 11 depicts an alternative coaxial cooling jacket within a one-piece side fire fiber cap where the shaped solid cylindrical element 500, similar to that depicted in FIG. 7C, is again fused within a relatively thinly walled quartz or silica tube 505 that is sealed 510 on the distal end like a test tube, capturing and preserving the air or partial vacuum 515 space that is required for total internal reflection at the TIR bevel 520. The outer diameter of the thin walled tube is machined to produce a pattern in relief 550 for centrosymmetric fusion to the inner diameter 525 of the heavier wall outer capsule 530, as well as an oval or round pad 535 for fusion that produces a uniform glass optical path for lateral emission and a balancing pad 540 for maintaining centricity in fusion. After fusing the inner wall 595 of the outer capsule 530 at the fusion pads 550, 535 and 540, the distal end of the outer capsule is substantially closed 560 leaving a coolant exhaust port 565 and the proximal end is step-chamfered 545 to mate with a complementary surface within a semi-rigid tube or cannula upon assembly into a side fire fiber device. The proximal end of the inner capsule may extend a millimeter or two 555 from the end of the outer capsule 570, or it may be cut flush with the end 570, depending upon what is preferable for sealing the transmitting optical fiber within the proximal void 580 (for coupling to the input lens surface 575 of the one-piece lateral delivery optical element). As with previous examples, coolant fluid, e.g. saline, is provided to the cap by a cannula where it flows between the machined outer diameter of the inner capsule 590 and the inner diameter of the outer capsule 595 within the voids 585 provided by the absence of glass about the spacing pads 550, output pad 535 and balancing pad to cool the device about the transmissive surface and exhausting via the distal port 565.

The degree of cooling provided in prior art devices is clearly better than no cooling, except where contaminated saline may cross the optical path, but prior art fibers continue to overheat. The GreenLight XPS™ laser incorporates "FiberLife", a safety system that detects when the fiber cap overheats and briefly interrupts the laser beam. Anecdotal reports from users indicate that "FiberLife" can be extremely frustrating due to the constant power interruptions required to keep the fiber cap cool at the full 180 watt output so many surgeons opt to use 120 watts to 140 watts instead. Additional means for removing heat, and/or for preventing heating are clearly needed.

In that heat drives the degradation process under the Devitrification Failure Cascade model, even incremental improvements in cooling may be of significant benefit. Heat removal rates are proportional to coolant flow rates but coolant flow is practicably limited for gravity feed in surgical applications, by the small dimensions of the fluid conduits within devices, and by less than optimal heat transfer due to the generally laminar flows within prior art devices. The embodiment depicted in FIG. 12 is directed at improving heat transfer by inducing turbulent flow for improved heat transfer from capsule to coolant.

FIG. 12 illustrates a far simpler to manufacture version of the concepts introduced in FIGS. 8 and 11, an embodiment that adds tortuosity to the coaxial coolant pathway within all areas of the one-piece side fire fiber capsule for improved heat transfer. As per the formula common to the other embodiments described, a TIR bevel is machined upon on end of a solid glass cylinder as depicted in FIG. 7B, but in this illustration a hollow cone 615 or concave lens is produced upon the opposing end for the purposes of expanding the beam imaged upon the transmitting surface by an inserted fiber conduit. The solid optical element akin to FIG. 7C is then fused within a thin-walled capillary and the end about the TIR bevel is sealed, similar to the construct depicted in FIG. 7D.

Rather than machine flats (FIG. 7E and FIG. 8) on the thin walled test tube (capillary) containing the solid optical element, two pair of helical grooves with opposite pitch are produced within the capillary wall in this embodiment, leaving small diamond, rectangular and large diamond shaped pads 600 in relief, one large diamond pad of which 605 is aligned with the optical output pathway. The thus patterned inner capsule is then positioned within a thicker wall, larger diameter capsule and the pads 600 are fused to the inner diameter of that larger tube. The larger tube is partially sealed producing a tortuous, multipath channel throughout the one-piece side firing capsule where the coolant is excluded from the optical path 610.

The high thermal conductivity of the silver protective cap of the VaporMAX™ prior art ('987) may offer significant protection against overheating by both protecting the glass capsule from direct tissue adhesion and by efficiently conducting heat away from the transmissive surface of the device. By coupling the silver cap to a long, steel cannula, VaporMAX also avoids the negative consequence of local heat displacement suffered by short metal cap designs such as DuoTome™. There is another negative consequence for using metal caps in side fire fibers designs for infrared lasers, however, related to the Moses bubble phenomenon.

Using the higher energy pulse settings available with most surgical holmium lasers, 5 joules per pulse, for example, a DuoTome fiber produces a best-case spot area on the transmissive surface of the glass capsule or approximately 0.01 square centimeters. The steel cap over the glass capsule is 0.25 mm thick. At typical divergence, the energy consumed in vaporizing the approximate conical frustum of fluid between the transmissive surface and the tissue, in contact with the steel cap, is roughly 0.4 joules: an 8% loss that is built into the fiber design. A means of reducing divergence in the emitted beam and/or reducing the thickness of the metal cap, bringing the transmissive surface closer to the tissue, would reduce the amount of energy lost in producing the steam vapor pathway.

Prior art water-cooled side fire fiber devices suffer similar losses to DuoTome in that a common coolant exit and laser exit necessitates some water column exist between the transmissive surface and the tissue; the coolant exit port must be defined by the existence of some thickness of outer covering about the transmissive surface in order to exist.

While heating in caps favors tissue adhesion, in turn, tissue adhesion within areas of the glass capsule that emit laser energy at irradiances lower than the tissue vaporization threshold generates heat. Blocking these emissions with a protective metal cap may prevent tissue adhesion directly upon the glass capsule for scattered emissions (those emissions that are artifacts of the device design, such as Fresnel reflections, or that result from less than optimum execution of the device design, such as TIR surface distortions in fusing beveled fiber tips within glass capsules), but metal caps cannot prevent tissue adhesion upon the glass capsule where the semi-Gaussian profiles of the emitted beams fall off to sub-vaporization threshold irradiance at the beam periphery.

Scatter that is blocked by metal caps continues to contribute to overheating by absorption of the scattered energy by the metal cap itself and even where tissue adhesion is not directly upon the glass capsule, tissue adhesion remains a concern. Tissue accumulations on metal caps can block clear visualization of the fiber position in the surgical field and may require fibers be removed and wiped clean periodically throughout a procedure. Blocking any portion of the emitted beam with steel results in rapid overheating of the device so "emission windows" within metal caps are typically significantly larger than the emitted beam, both to facilitate alignment in assembly and reduce the potential for blocking the beam.

Most prior art side fire fibers present non-circular output spots (projections of the laser output beam upon the transmissive surface). "Fused fibers" are a subclass of side fire fibers where the cylindrical output surface of the beveled fiber tips is joined to the inside surface of the surrounding protective (glass) cap. The output spot of fused fibers can be relatively free of distortion (new) where the fusion process is well controlled, minimizing melting and warping of the TIR surface, and appear generally elliptical (when projected on a target some distance removed from the transmissive surface). Fusion is relatively simple to accomplish in the case of MoXy™ (FIG. 6), where the glass capsule wall 170 is relatively thin (approximately 0.15 mm) and the fiber glass cladding 157 is relatively large (approximately 0.825 mm), such that a new MoXy fiber produces a relatively distortion-free output (similar to FIG. 3B). The inverse is the case for DuoTome™ (FIG. 2), where a thicker wall (approximately 0.7 mm) glass capsule 60 is fused upon the cladding 55 of a thinner fiber (approximately 0.6 mm) where a distorted output (FIG. 3A) is inevitable. All currently marketed side fire fibers for infrared lasers are fused output designs.

Most prior art side fire fiber optical designs suffer considerable scatter, e.g. the model 2090 fiber emits roughly 90% of the laser energy in the desired direction with balance of energy scattered generally in the opposite direction, even the fused designs like DuoTome and Laser Peripherals' 'Scatterfree' side fire fiber, although fused fibers' scatter is typically forward such that it is included in most measurements of efficiency. As is the practice in the field of art, a side fire fiber device such as model 2090 is said to be 90% efficient (or 90% transmission (% T)) when new. Lower initial % T designs typically heat faster and to higher temperatures than higher % T fibers, but % T is not the sole measure that predicts fiber longevity, especially now that most side fire fiber designs involve fusion.

Tissue adhesion about the periphery of the output spot generally contributes more to fiber destruction than adhesion to areas of the glass capsule where scatter exits, or where scatter is absorbed for metal sleeved devices. It follows that larger areas of tissue adhesion about the transmissive window generate more heat. Minimization of the area where tissue adhesion is favored is a fundamental design goal within the tenets of the Devitrification Failure Cascade model.

Typical side fire fibers that are based upon total internal reflection principles are limited to turning the laser output to somewhat less than 90 degree relative to the longitudinal axis of the fiber by common optical properties and principles: Snell's law, the indices of refraction of the materials used and the numerical aperture of the base fiber optic material. Such side fire fibers maximum off-axis angle (measured at the central ray of the emission, or geometric center of a projected spot and referred to as "firing angle", "output angle" or "emission angle") is further limited by the realities reproducibility for precise angles machined on small strands of glass. Lumenis specifies the DuoTome™ output angle FIG. 3A at 70 degrees while AMS specifies the MoXy™ at 70 degrees to 80 degrees: both prior art fibers produce an elliptical spot on the transmissive surface as a result. For reference, the LDD75 output angle is 75 degrees FIG. 3B.

The elliptical distortion in less than orthogonal outputs increases both the area of the output spot and its perimeter: irradiance is reduced and there is a larger area favoring tissue adhesion. The output of non-orthogonal side fire fibers is further complicated by the curvature of the transmissive surface, giving rise to differing divergences oriented along the axes of the elliptical spot and tissue adhesion is favored distal to the output spot due to a wider perimeter where irradiance is below the vaporization threshold (as seen in the accumulated tissue/devitrification in the box marked 7 on the model 2090 transmissive surface in FIG. 5A).

Accordingly, a second parameter that is predictive of fiber longevity is spot geometry and a third predictive parameter is spot uniformity: the rounder and more uniform the output spot, the slower the onset and progression of devitrification. It should be noted that all three of these metrics may also be used in evaluating the extent of damage suffered by a fiber during use.

Still another embodiment is a termination for an optical fiber that includes a tube portion comprising an optical emission surface; an optical element contained within the tube portion that includes an unbroken light path from an input surface to the optical emission surface, the optical element further including a reflecting surface configured to laterally redirect electromagnetic radiation from the input surface to the optical emission surface; and a devitrification inhibitor configured to prevent devitrification of the tube portion and/or the optical element. In one instance, the devitrification inhibitor can include a thermal element configured to cool the optical element and the tube portion without interrupting the light path. In another instance, the devitrification inhibitor can include a confined flow passageway for transfer of a cooling medium through the tube portion. Preferably, the confined flow passageway is configured to exclude the cooling medium from the light path.

Yet another embodiment is a process of prolonging an output quality for a side-fire fiber. Herein, the output quality is a measure of the initial beam shape and power. In one instance, the degradation of the output quality can be attributed to the devitrification of the termination of the side-fire fiber. In another instance, the degradation can be attributed to pitting of an output surface. In still another instance, the degradation can be attributed to the adhesion of tissue to the output surface. This process can include providing a termination for an optical fiber that includes a lateral redirection of a light path from in-put optical fiber to an output surface; passing a cooling fluid through a confined flow passageway within the termination, wherein a cooling fluid flow path does not intersect the light path; thereby reducing degradation of an output signal. Notably, the reduction of the degradation of the output signal is an effect of the cooling fluid passing through the confined flow passageway within the termination.

In one example, the degradation of the output signal efficiency is determined by beam profile analysis. In one instance, the width of the X and the Y beam profile, individually, change by less than 20%, 15%, or 10% following surgical use of the side-fire fiber. In another example, distortion of the output spot is less than 20%, 15%, or 10% of the side-fire fiber prior to surgical use. The output spot distortion can be determined by spot area or irradiance maxima (from a predetermined maximum).

In another example, the termination for the optical fiber can be as described above, for example including a tube portion comprising a fluid emission aperture and an optical emission surface; an optical element contained within the tube portion that includes an unbroken light path from an input surface to the optical emission surface, the optical element further including a reflecting surface configured to direct electromagnetic radiation from the input surface to the optical emission surface; and a confined flow passageway for transfer of a fluidic medium through the tube portion to the fluid emission aperture, the confined flow passageway adjacent to the optical element but external to the light path. Preferably, the reflecting surface is external to the confined flow passageway.

Here, the termination can include a plurality of confined flow passageways which do not intersect the light path. In one instance, these confined flow passageways include helical grooves carried on an external surface of the optical element.

Preferably, the termination includes an optical element has a one-piece construction consisting of fused quartz and/or fused silica. In one instance, the optical element can include a guide section and an open-end section. The open-end section and the guide section divided by the input surface. The open-end section including a bore which terminates at the input surface. The open-end section shaped to receive a fiber optic cable; and where the guide section including at least a portion of the unbroken light path. In a preferable instance, the optical element is fused to an internal surface of the tube portion. In this instance, at least a portion of the confined flow passageway can be defined as a volume between the optical element and the internal surface of the tube portion. Another instance includes an optical fiber affixed to the optical element; the optical fiber having an output surface adjacent to the input surface of the optical element.

In another instance, the tube portion and the optical element are a one piece construction consisting of fused quartz and/or fused silica. That is, the tube portion and the optical element are or consist of a fused quartz or silica object. Notably, quartz and silica can be assembled from different parts, joined, and fused to yield a single final object.

In still another instance, the optical element includes an optical fiber, the optical fiber carrying the reflecting surface as a beveled termination and having an input surface distal from the beveled termination, the optical element further including a quartz or silica capsule, the silica capsule disposed about the beveled termination. Preferably, the silica capsule is fused to an internal surface of the tube portion. In one example, an optical pathway extends within the optical fiber from an optical fiber input to an optical fiber output, from the optical fiber output to the input surface, and includes the unbroken light path of the optical element. Preferably, this optical pathway is external to the confined flow passageway.

In another example, the cooling fluid in the process includes saline. As described above, saline is used herein to mean any physiologically compatible, aqueous irrigation or perfusion fluid that is generally known in the practice of medicine, including Ringer's and simple sugar solutions.

In another preferably example, the cooling fluid maintains a working temperature for the termination during use. More preferably, the cooling fluid does not boil or convert to a gaseous phase while passing through the confined flow passageway.

Yet another embodiment is a laser surgical process that includes providing a termination for an optical fiber that includes a lateral redirection of a light path; cooling the termination by passing a cooling fluid through a confined flow passageway within the termination; and preventing Moses Bubble formation within the termination. In this embodiment, the termination for the optical fiber can include a tube portion comprising a fluid emission aperture and an optical emission surface; an optical element contained within the tube portion that includes an unbroken light path from an input surface to the optical emission surface, the optical element further including a reflecting surface configured to direct electromagnetic radiation from the input surface to the optical emission surface; and a confined flow passageway for transfer of a fluidic medium through the tube portion to the fluid emission aperture, the confined flow passageway adjacent to the optical element but external to the light path.

In one example, the termination for the optical fiber can be as described above, for example including a tube portion comprising a fluid emission aperture and an optical emission surface; an optical element contained within the tube portion that includes an unbroken light path from an input surface to the optical emission surface, the optical element further including a reflecting surface configured to direct electromagnetic radiation from the input surface to the optical emission surface; and a confined flow passageway for transfer of a fluidic medium through the tube portion to the fluid emission aperture, the confined flow passageway adjacent to the optical element but external to the light path. Preferably, the reflecting surface is external to the confined flow passageway.

Alternatively, the termination can include a plurality of confined flow passageways which do not intersect the light path. In one instance, these confined flow passageways include helical grooves carried on an external surface of the optical element.

Preferably, the termination includes an optical element has a one-piece construction consisting of fused quartz and/or fused silica. In one instance, the optical element can include a guide section and an open-end section. The open-end section and the guide section divided by the input surface. The open-end section including a bore which terminates at the input surface. The open-end section shaped to receive a fiber optic cable; and where the guide section including at least a portion of the unbroken light path. In a preferable instance, the optical element is fused to an internal surface of the tube portion. In this instance, at least a portion of the confined flow passageway can be defined as a volume between the optical element and the internal surface of the tube portion. Another instance includes an optical fiber affixed to the optical element; the optical fiber having an output surface adjacent to the input surface of the optical element.

In another instance, the tube portion and the optical element are a one piece construction consisting of fused quartz and/or fused silica. That is, the tube portion and the optical element are or consist of a fused quartz or silica object. Notably, quartz and silica can be assembled from different parts, joined, and fused to yield a single final object.

In still another instance, the optical element includes an optical fiber, the optical fiber carrying the reflecting surface as a beveled termination and having an input surface distal from the beveled termination, the optical element further including a quartz or silica capsule, the silica capsule disposed about the beveled termination. Preferably, the silica capsule is fused to an internal surface of the tube portion. In one example, an optical pathway extends within the optical fiber from an optical fiber input to an optical fiber output, from the optical fiber output to the input surface, and includes the unbroken light path of the optical element. Preferably, this optical pathway is external to the confined flow passageway.

This laser surgical process can further include providing the optical fiber, wherein the optical fiber is adapted to provide a surgical laser. Preferably, wherein the optical fiber and the termination are provided as a single unit or piece.

Still further this laser surgical process can include irradiating a target with the surgical laser through the termination while cooling the termination. That is, the process includes the surgical application of the herein described terminations and optical fibers.

Still another embodiment is a laser surgical process that can include providing a termination for an optical fiber that includes a lateral redirection of a light path; the termination including a tube portion comprising a fluid emission aperture and an optical emission surface, an optical element contained within the tube portion that includes an unbroken light path from an input surface to the optical emission surface, the optical element further including a reflecting surface configured to direct electromagnetic radiation from the input surface to the optical emission surface, and a confined flow passageway for transfer of a fluidic medium through the tube portion to the fluid emission aperture, the confined flow passageway adjacent to the optical element but external to the light path; and cooling the termination by passing a cooling fluid through a confined flow passageway within the termination.

Variations that do not greatly impact the form or function of the embodiments disclosed will be apparent to those skilled in the art as well as refinements of potential benefit, e.g. alternative locations for coolant exit. The embodiments disclosed are meant to be illustrative of the concepts taught in this disclosure and are not limiting.

What is claimed:

1. A termination for an optical fiber comprising:
   a tube portion comprising a fluid emission aperture and an optical emission surface;
   an optical element contained within the tube portion that includes an unbroken light path from an input surface to the optical emission surface, the optical element further including a reflecting surface configured to direct electromagnetic radiation from the input surface to the optical emission surface; and
   a confined flow passageway for transfer of a fluidic medium through the tube portion to the fluid emission aperture, the confined flow passageway adjacent to the optical element but external to the light path;
   wherein the tube portion and the optical element are a one piece construction consisting of fused quartz and/or fused silica.

2. The termination of claim 1 further comprising a plurality of confined flow passageways which do not intersect the light path.

3. The termination of claim 2, wherein the confined flow passageways include helical grooves carried on an external surface of the optical element.

4. The termination of claim 1, wherein the optical element has a one-piece construction consisting of fused quartz and/or fused silica.

5. The termination of claim 4, wherein the optical element includes a guide section and an open-end section, the open-end section and the guide section divided by the input surface, the open-end section including a bore which terminates at the input surface, the open-end section shaped to receive a fiber optic cable, the guide section including at least a portion of the unbroken light path.

6. The termination of claim 4, wherein the optical element is fused to an internal surface of the tube portion.

7. The termination of claim 6, wherein at least a portion of the confined flow passageway is defined as a volume between the optical element and the internal surface of the tube portion.

8. The termination of claim 4 further comprising an optical fiber affixed to the optical element, the optical fiber having an out-put surface adjacent to the input surface of the optical element.

9. The termination of claim 1, wherein the reflecting surface is external to the confined flow passageway.

10. A termination for an optical fiber comprising:
    a tube portion comprising an optical emission surface;
    an optical element contained within the tube portion that includes an unbroken light path from an input surface to the optical emission surface, the optical element further including a reflecting surface configured to laterally redirect electromagnetic radiation from the input surface to the optical emission surface; and
    a devitrification inhibitor configured to prevent devitrification of the tube portion and/or the optical element;
    wherein the tube portion and the optical element are a one piece construction consisting of fused quartz and/or fused silica.

11. The termination of claim 10, wherein the devitrification inhibitor includes a confined flow passageway for transfer of a cooling medium through the tube portion.

12. The termination of claim 11, wherein the confined flow passageway is configured to exclude the cooling medium from the light path.

13. A termination for an optical fiber comprising:
    a tube portion comprising a fluid emission aperture and an optical emission surface;
    an optical element contained within the tube portion, the optical element including an optical fiber, the optical fiber carrying a reflecting surface as a beveled termination and having an input surface distal from the beveled termination, the reflecting surface configured to direct electromagnetic radiation from the input surface to the optical emission surface, the optical element further including a quartz or silica capsule, the quartz or silica capsule disposed about the beveled termination; and
    a confined flow passageway for transfer of a fluidic medium through the tube portion to the fluid emission aperture, the confined flow passageway adjacent to the optical element but external to the light path;
    wherein the tube portion and the capsule are a one piece construction consisting of fused quartz and/or fused silica.

14. The termination of claim 13 further comprising an optical pathway extending within the optical fiber from an optical fiber input to an optical fiber output, from the optical fiber output to the input surface; wherein the optical pathway is external to the confined flow passageway.

15. The termination of claim 13, wherein the capsule carries a flat or channel along an entire length of the capsule; wherein the flat or channel is at least one side of the confined flow passageway.

* * * * *